United States Patent
Zheng et al.

(10) Patent No.: US 11,684,716 B2
(45) Date of Patent: Jun. 27, 2023

(54) TECHNIQUES TO REDUCE RISK OF OCCLUSIONS IN DRUG DELIVERY SYSTEMS

(71) Applicant: Insulet Corporation, Acton, MA (US)

(72) Inventors: Yibin Zheng, Hartland, WI (US); Joon Bok Lee, Acton, MA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 393 days.

(21) Appl. No.: 16/945,246

(22) Filed: Jul. 31, 2020

(65) Prior Publication Data

US 2022/0031944 A1    Feb. 3, 2022

(51) Int. Cl.
| | |
|---|---|
| *A61M 5/172* | (2006.01) |
| *A61M 5/142* | (2006.01) |
| *A61K 38/28* | (2006.01) |
| *G16H 20/17* | (2018.01) |
| *G16H 40/67* | (2018.01) |
| *G05D 7/06* | (2006.01) |
| *G05B 15/02* | (2006.01) |

(52) U.S. Cl.
CPC .............. *A61M 5/172* (2013.01); *A61K 38/28* (2013.01); *A61M 5/14248* (2013.01); *G05B 15/02* (2013.01); *G05D 7/0623* (2013.01); *G05D 7/0676* (2013.01); *G16H 20/17* (2018.01); *G16H 40/67* (2018.01); *A61M 2205/18* (2013.01); *A61M 2205/3331* (2013.01); *A61M 2205/3584* (2013.01); *A61M 2205/52* (2013.01)

(58) Field of Classification Search
None
See application file for complete search history.

(56) References Cited

U.S. PATENT DOCUMENTS

| | | |
|---|---|---|
| 303,013 A | 8/1884 | Horton |
| 2,797,149 A | 6/1957 | Skeggs |
| 3,631,847 A | 1/1972 | Hobbs |
| 3,634,039 A | 1/1972 | Brandy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |

(Continued)

FOREIGN PATENT DOCUMENTS

| | | |
|---|---|---|
| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Manuel A Mendez
(74) *Attorney, Agent, or Firm* — Goodwin Procter LLP

(57) ABSTRACT

Disclosed are techniques to establish a modified pump rate that mitigates the effects of a pump occlusion and enables a recommended dosage of insulin to be output by a pump mechanism over the course of a control cycle. In an example, the pump rate may be reduced by adding a calculated time interval between application of actuation commands to extend the amount of time over which insulin may be output by the pump mechanism.

20 Claims, 7 Drawing Sheets

(56) References Cited

U.S. PATENT DOCUMENTS

| | | |
|---|---|---|
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,484,044 A | 1/1996 | Bursteinas |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Komerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |

(56) References Cited

U.S. PATENT DOCUMENTS

| | | |
|---|---|---|
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Frepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko et al. |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |

(56) References Cited

U.S. PATENT DOCUMENTS

| | | |
|---|---|---|
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |

(56) References Cited

U.S. PATENT DOCUMENTS

| | | |
|---|---|---|
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla et al. |
| 2012/0282111 A1 | 11/2012 | Nip et al. |
| 2012/0295550 A1 | 11/2012 | Wilson et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 9801578 B1 | 7/2006 |
| EP | 2666520 A1 | 10/2009 |
| EP | 2139382 A1 | 1/2010 |
| EP | 2397181 A1 | 12/2011 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |

(56) References Cited

FOREIGN PATENT DOCUMENTS

| | | | |
|---|---|---|---|
| WO | 2006053007 A2 | 5/2006 | |
| WO | 2007064835 A2 | 6/2007 | |
| WO | 2007078937 A1 | 7/2007 | |
| WO | 2008024810 A2 | 2/2008 | |
| WO | 2008029403 A1 | 3/2008 | |
| WO | 2008133702 A1 | 11/2008 | |
| WO | 2009045462 A1 | 4/2009 | |
| WO | 2009049252 A1 | 4/2009 | |
| WO | 2009066287 A3 | 5/2009 | |
| WO | 2009066288 A1 | 5/2009 | |
| WO | 2009098648 A2 | 8/2009 | |
| WO | 2009134380 A2 | 11/2009 | |
| WO | 2010053702 A1 | 5/2010 | |
| WO | 2010132077 A1 | 11/2010 | |
| WO | 2010138848 A1 | 12/2010 | |
| WO | 2010147659 A2 | 12/2010 | |
| WO | 2011095483 A1 | 8/2011 | |
| WO | 2012045667 A2 | 4/2012 | |
| WO | 2012108959 A1 | 8/2012 | |
| WO | 2012134588 A1 | 10/2012 | |
| WO | 2012177353 A1 | 12/2012 | |
| WO | 2012178134 A2 | 12/2012 | |
| WO | 2013078200 A1 | 5/2013 | |
| WO | 2013134486 A2 | 9/2013 | |
| WO | 20130149186 A1 | 10/2013 | |
| WO | 2013177565 A1 | 11/2013 | |
| WO | 2013182321 A1 | 12/2013 | |
| WO | 2014109898 A1 | 7/2014 | |
| WO | 2014110538 A1 | 7/2014 | |
| WO | 2014194183 A2 | 12/2014 | |
| WO | 2015056259 A1 | 4/2015 | |
| WO | 2015061493 A1 | 4/2015 | |
| WO | 2015073211 A1 | 5/2015 | |
| WO | 2015081337 A2 | 6/2015 | |
| WO | 2015187366 A1 | 12/2015 | |
| WO | 2016004088 A1 | 1/2016 | |
| WO | 2016022650 A1 | 2/2016 | |
| WO | 2016041873 A1 | 3/2016 | |
| WO | 2016089702 A1 | 6/2016 | |
| WO | 2016141082 A1 | 9/2016 | |
| WO | 2017004278 A1 | 1/2017 | |
| WO | 2017091624 A1 | 6/2017 | |
| WO | 2017105600 A1 | 6/2017 | |
| WO | 2017205816 A1 | 11/2017 | |
| WO | 2018009614 A1 | 1/2018 | |
| WO | 2018067748 A1 | 4/2018 | |
| WO | WO-2018093727 A1 * | 5/2018 | ............ A61M 5/172 |
| WO | 2018120104 A1 | 7/2018 | |
| WO | 2018136799 A1 | 7/2018 | |
| WO | 2018204568 A1 | 11/2018 | |
| WO | 2019077482 A1 | 4/2019 | |
| WO | 2019094440 A1 | 5/2019 | |
| WO | 2019213493 A1 | 11/2019 | |
| WO | 2019246381 A1 | 12/2019 | |
| WO | 2020081393 A1 | 4/2020 | |
| WO | 2021011738 A1 | 1/2021 | |

OTHER PUBLICATIONS

European Search Report for the European Patent Application No. 21168591.2, dated Oct. 13, 2021, 04 pages.
International Search Report and Written Opinion for the International Patent Application No. PCT/US2021/041954, dated Oct. 25, 2021, 13 pages.
International Search Report and Written Opinion for the International Patent Application No. PCT/US2021/047771, dated Dec. 22, 2021, 11 pages.
International Search Report and Written Opinion for the International Patent Application No. PCT/US2021/052855, dated Dec. 22, 2021, 11 pages.
Unger, Jeff, et al., "Glucose Control in the Hospitalized Patient," Emerg. Med 36(9):12-18 (2004).
Glucommander FAQ downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, dated Jun. 2, 2021, 15 pages.
Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.
Davidson, Paul C., et al., A computer-directed intravenous insulin system shown to be safe, simple,and effective in 120,618 h of operation. Diabetes Care, vol. 28, No. 10, Oct. 2005, pp. 2418-2423.
Gorke, A. "Microbial contamination of haemodialysis catheter connections." EDTNA/ERCA journal (English ed.) vol. 31,2 (2005): 79-84. doi:10.1111/j.1755-6686.2005.tb00399.x.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al, "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010 (OPTIS.247VPC).
International Search Report and Written Opinion in PCT/US2008/079641 (Optis.203VPC) dated Feb. 25, 2009.
Berger, ""Measurement of Analytes in Human Serum and Whole Blood Samples by Near-Infrared Raman Spectroscopy,"" Ph D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 323-627, Feb. 1, 1998.
Billman et al.,"Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.

(56) References Cited

OTHER PUBLICATIONS

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
European Patent Office, "Notification of Transmittal of the ISR and the Written Opinion of the International Searching Authority, or the Declaration," in PCT Application No. PCT/GB2015/050248, dated Jun. 23, 2015, 12 pages.
An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.
International Search Report and Written Opinion for the International Patent Application No. PCT/US2021/017441, dated May 25, 2021, 12 pages.
International Search Report and Written Opinion for the InternationalPatent Application No. PCT/US2021/017664, dated May 26, 2021, 16 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, dated May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, dated May 27, 2021, 16 pages.
International Search Report and Written Opinion for the International Patent Application No. PCT/US2020/065226, dated May 31, 2021, 18 pages.
International Search Report and Written Opinion for the International Patent Application No. PCT/US2021/017659, dated May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
International Search Report and Written Opinion for Application No. PCT/US2019/030562, dated Sep. 25, 2019, 19 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, dated Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018, 12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
International Search Report and Written Opinion for Application No. PCT/US2019/030652, dated Sep. 25, 2019, 19 pages.

(56) References Cited

OTHER PUBLICATIONS

International Search Report and Written Opinion for the International Patent Application No. PCT/US2022/013470, dated May 6, 2022, 14 pages.
International Search Report and Written Opinion for the International Patent Application No. PCT/US2022/013473, dated May 6, 2022, 13 pages.
International Search Report and Written Opinion for the International Patent Application No. PCT/US2022/019079, dated Jun. 2, 2022, 14 pages.
International Search Report and Written Opinion for the International Patent Application No. PCT/US2022/018453, dated Jun. 2, 2022, 13 pages.
International Search Report and Written Opinion for the International Patent Application No. PCT/US22/018700, dated Jun. 7, 2022, 13 pages.
International Search Report and Written Opinion for the International Patent Application No. PCT/US22/019080, dated Jun. 7, 2022, 14 pages.
International Search Report and Written Opinion for the International Patent Application No. PCT/US22/019664, dated Jun. 7, 2022, 14 pages.
International Search Report and Written Opinion for the International Patent Application No. PCT/US21/060618, dated Mar. 21, 2022, 15 pages.
Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernnel_density_estimation&oldid=988508333 [retrieved on Jun. 6, 2022].
Anonymous: "openaps / oref0 /lib/determine-basal-js", openaps repository, Nov. 9, 2019 (Nov 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, dated Apr. 22, 2022, 15 pages.
Kohdaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190.
International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.
International Search Report and Written Opinion for the International Patent Application No. PCT/US2021/055745, dated Feb. 14, 2022, 13 pages.

* cited by examiner

100

```
┌─────────────────────────────────────────────┐
│ Receive a control instruction to deliver a  │
│ dosage of insulin                           │    110
└─────────────────────────────────────────────┘
                      │
                      ▼
┌─────────────────────────────────────────────┐
│ Modify a pump rate for delivery of the      │
│ dosage by at least adding additional time   │    120
│ to a preset time period for delivering the  │
│ dosage of insulin                           │
└─────────────────────────────────────────────┘
                      │
                      ▼
┌─────────────────────────────────────────────┐
│ Output an actuation command to actuate a    │
│ pump to output the dosage of insulin        │    130
│ included in the control instruction at the  │
│ modified pump rate                          │
└─────────────────────────────────────────────┘
```

510 — Receive a pressure sensor signal from a pressure sensor in a fluid delivery path through which the dosage of insulin is delivered, wherein the received pressure sensor signal includes a pressure value 520 — Determine whether the pressure value exceeds a threshold 530 — In response to the determination that the pressure value exceeds the threshold, access a lookup table containing pressure values with corresponding additional time increments to select an additional time increment to be added to the preset time period 540 — Use the additional time increment in the modification of the pump rate

563 — Receive the pressure sensor signal from the pressure sensor coupled to a fluid delivery path through which the dosage of insulin is output 573 — Based on the received pressure sensor signal, calculate an amount of delivery back pressure 583 — Determine whether the calculated amount of delivery back pressure exceeds a threshold 593 — Based on the result of the determination, generate an indication that the delivery pressure value has increased

FIG. 5B

TECHNIQUES TO REDUCE RISK OF OCCLUSIONS IN DRUG DELIVERY SYSTEMS

BACKGROUND

Subcutaneous insulin delivery is the most commonly utilized, minimally invasive method of insulin delivery for people with Type-1 diabetes mellitus (T1DM) that utilize insulin pumps. Unfortunately, subcutaneous insulin infusion incurs a wide range of risks that must be mitigated to ensure safety of the users. One of the most critical risks is pump occlusion, which can be defined as insulin delivery from the pump being impeded from actual delivery into the body, potentially caused by site pressure, scar tissue formation, incorrect cannula insertion, and others.

It is known that a high rate of insulin infusion is strongly correlated with increased incidence of pump occlusions. This is due to issues in subcutaneous insulin infusion sites potentially reducing in the rate of absorption of the subcutaneously delivered insulin into the bloodstream and increasing the resistance (back pressure) against additional insulin delivery. This resistance against additional insulin delivery is exacerbated with high insulin delivery rates, as the back pressure does not have sufficient time to be absorbed by a user's body before additional insulin is delivered into the infusion site.

This back pressure issue is especially apparent during a user-initiated "bolus" insulin delivery of pump users, where the pump attempts to deliver an insulin dosage greater than normal and at a fixed rate possible upon user request.

It would be advantageous to provide techniques and devices operable to mitigate the effects a pump occlusion on the delivery of drugs to a user.

SUMMARY

Disclosed is an example of a non-transitory computer readable medium embodied with programming code executable by a processor. When the programming code is executed by the processor, the processor may be operable to receive a control instruction to deliver a dosage of insulin. The control instruction may include an amount of insulin to be output as the dosage of insulin. A pump rate for delivery of the dosage of insulin may be modified by adding additional time to a preset time period to provide an extended time period for outputting the dosage of insulin. An actuation command may be to output to actuate a pump mechanism to output the dosage of insulin included in the control instruction at the modified pump rate.

An example of a drug delivery device is disclosed that includes a reservoir, a cannula, a pump mechanism, a memory, a controller and a communication device. The reservoir may be configured to hold a liquid drug. The cannula may be coupled to the reservoir via a fluid delivery path and operable to output the liquid drug to a user. The pump mechanism may be coupled to the reservoir and operable to output the liquid drug from the reservoir via the fluid delivery path and out of the cannula. The memory may be operable to store programming code, applications including a delivery control application, and data. The controller may be coupled to the pump mechanism and the memory, and operable to execute programming code and the applications including the delivery control application. The communication device may be operable to wirelessly communicate with an external device and communicatively coupled to the controller. The controller, when executing the delivery control application, may be operable to receive, from the external device, a control instruction including a dosage of insulin to be output by the pump mechanism. The received control instruction may indicate an amount of insulin to be output for a control cycle. The controller may be operable to calculate an output distribution of the dosage of insulin by the pump mechanism. The output distribution may be a series of partial insulin doses output at discrete times distributed over the control cycle. An actuation command may be output by the controller to actuate the pump mechanism to deliver a partial each insulin dose in the series of partial insulin doses.

An example of a method is also disclosed that may include receiving a control instruction to deliver a dosage of insulin. The control instruction may include a dosage of insulin to be output as a pump mechanism. A number of doses of insulin may be determined to be delivered based on a duration of a control cycle. The sum of the number of doses of insulin may equal the dosage of insulin, to be delivered based on a duration of a control cycle. A series of actuation commands may be output. The series of actuation commands may include a number of actuation commands equal to a number of doses of insulin in the plurality of doses of insulin. Each actuation command in the series of actuation commands may actuate a pump mechanism to output a respective dose of insulin of the plurality of doses of insulin, and each actuation command may be applied after passage of a selected additional time period based on the duration of the control cycle.

BRIEF DESCRIPTION OF THE DRAWINGS

FIG. 1 illustrates an example of a process for modifying a pump rate for delivery of a dosage of insulin.

FIG. 5A illustrates an example of a process for detecting a pump occlusion that may result in a modification of a pump rate.

FIG. 5B illustrates an example of a process for detecting a pump occlusion that may result in a modification of a pump rate.

DETAILED DESCRIPTION

Figure 2:
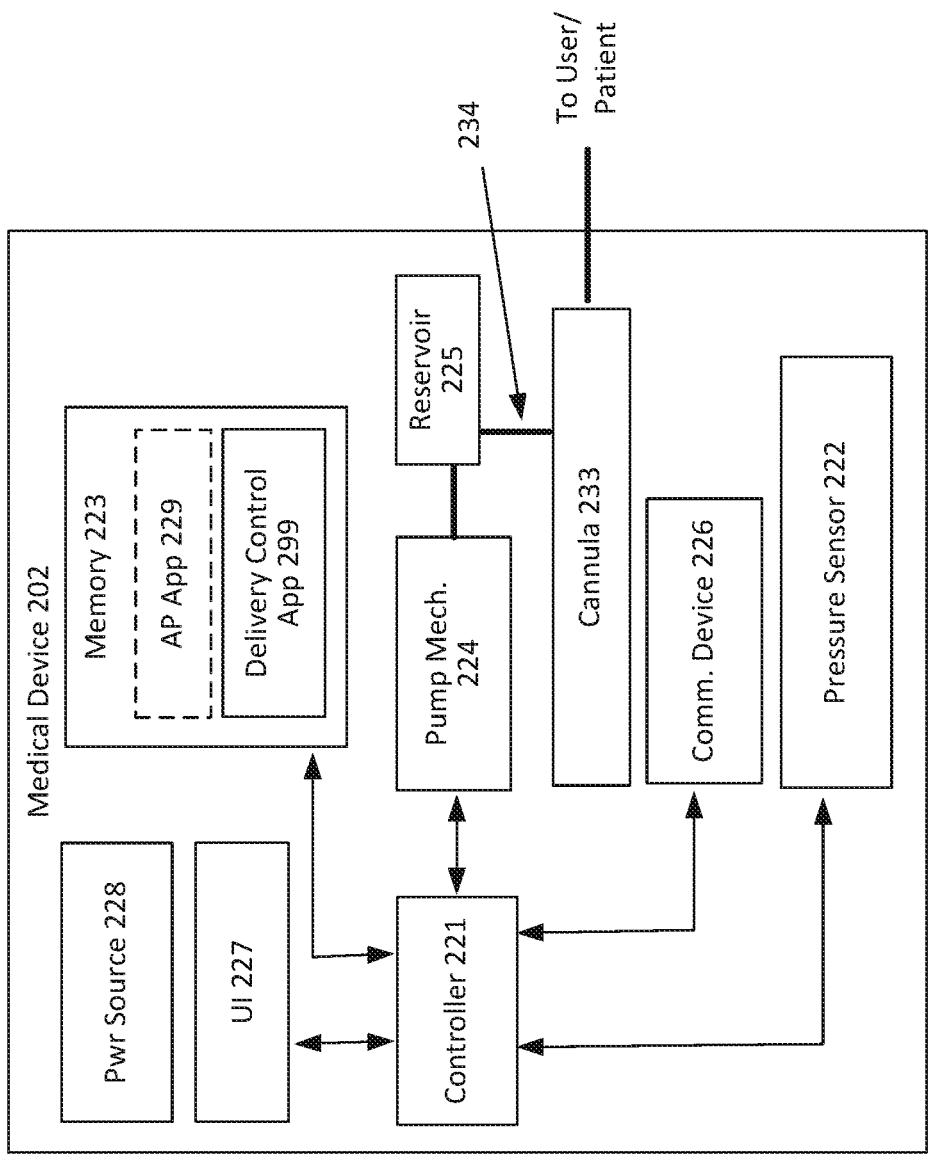
FIG. 2 illustrates an example of a functional block diagram of drug delivery system suitable for implementing the example processes and techniques described herein.

An example provides a process that may be used with additional algorithms or computer applications that may provide information and enable management of blood glucose levels and insulin therapy. Such algorithms may include an "artificial pancreas" algorithm-based system, or more generally, an artificial pancreas (AP) application or automatic insulin delivery (AID) algorithm, that provides automatic delivery of insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered within a threshold value of a target blood glucose value of the particular user. For example, a target blood glucose value may be acceptable if it falls within the range of 80 mg/dL to 120 mg/dL, which is a range satisfying the clinical standard of care for treatment of diabetes. Alternatively, in addition, an AP application (or AID algorithm) as described herein may be able to establish a target blood glucose value more precisely and may set the target blood glucose value at, for example, 110 mg/dL, or the like. As described in more detail with reference to the examples of FIGS. 1-5, the AP application (or AID algorithm) may utilize the monitored blood glucose measurement values and other information to determine an optimal pump rate that mitigates potential causes of insulin device pump occlusions, or the like. A pump rate may be the amount of insulin that may be output by a pump over a set period of time.

In operation, a wearable drug delivery device (also referred to as "a drug delivery device" herein) may be affixed at a site on a user's body, such as, for example, the abdomen or upper arm. The drug delivery device may include a needle insertion component, a needle and a flexible cannula within the needle, a reservoir containing insulin, a pump that is a mechanism operable to expel various amounts of insulin from the reservoir, and control logic circuitry that is operable to control the pump and delivery of insulin from the reservoir to the flexible cannula. A needle may be used to puncture the user's skin to the depth of subcutaneous tissue, and within the needle is a flexible cannula. After puncturing the user's skin, the needle is withdrawn leaving the flexible cannula in place. Insulin may be delivered from the reservoir based on the pump causing insulin to be expelled from the reservoir to a fluid delivery path that leads to the flexible cannula that has been inserted in the user's body.

In operation, the wearable drug delivery device may be operable to deliver a basal dosage of insulin and a bolus amount of insulin. The basal dosage of insulin is a small amount of insulin that is gradually delivered to a user over the course of a day (i.e., 24 hours). A bolus is an amount of insulin greater than the basal dosage that is delivered in a much shorter period of time than the extended period of time over which the basal dosage is delivered. A bolus dosage may be requested or required for various reasons, most typically, a bolus dosage is delivered in response to the consumption of a meal by the user, but also in response to exercise or as a way to correct excursions of the user's blood glucose measurements. The sum of the insulin amounts delivered as a basal dosage and in the bolus dosages may be referred to as the user's total daily insulin (TDI). The AID algorithm may be operable to deliver basal dosages, bolus dosages as well as other dosages, that are greater than a basal dosage but less than a typical bolus dosage. These other dosages may be referred to as "microboluses." A microbolus may be an amount of insulin greater than basal but less than a bolus. In an example, the amount of insulin in a microbolus may include the amount of insulin in the basal dosage. If the user's blood glucose is within the "safe range," such as 70 mg/dL-120 mg/dL, the amount of insulin contained in the microbolus may be substantially equal to the basal dosage of insulin. Microboluses may be less likely to be occluded because it is smaller than a typical bolus dosage.

In some instances, a situation may arise during which a proper amount of insulin is not delivered to a user within a predetermined time period. The predetermined time period may be referred to as "a control cycle." A common cause of the non-delivery (e.g., an improper delivery) of the intended amount of insulin within the predetermined amount of time is the presence of what is generally referred to as a pump occlusion. A pump occlusion may be defined as insulin delivery from the pump being impeded from actual delivery into the body. The occlusion may be within a pump mechanism, a fluid delivery path of the medical device, a needle or cannula, or the user's body. A non-delivery of insulin is intended to mean that an intended amount of insulin was not delivered to the user for some reason, such as a pump occlusion. In the disclosed examples, a control cycle may be approximately 5 minutes. Of course, the control cycle may be a period of time that is longer or shorter than approximately 5 minutes, such as 3 minutes, 6.5 minutes or the like. In an example, control logic circuitry in a pump may initiate delivery of a predetermined amount of insulin that is to be delivered to the user within a set period of time, e.g., 30 seconds. The control logic circuitry may direct the pump to deliver the predetermined amount of insulin within the set period of time, but due to a pump occlusion, the pump may be unable to complete the delivery of the predetermined amount of insulin within the set period of time.

However, there may be times that an intended amount, or proper dosage, of insulin is not delivered to the user, which may be referred to as a non-delivery or improper delivery. A pump occlusion may be caused by various conditions. In a first example, the drug delivery device may be deployed with the flexible cannula inserted in the user. The deployed drug delivery device while initially affixed to a site on a user may shift which may result in movement of the drug delivery device. However, the flexible cannula cannot move since the flexible cannula is inserted in the user. This relative movement between the drug delivery device and the flexible cannula may cause a kink in the flexible cannula. As a result of the kink, the full amount of the predetermined amount of insulin may not be delivered within the set period of time.

In a second example, pressure may be applied on a surface of the drug delivery device (such as the top or the side) and consequently to the site of the body at which the drug delivery device is located. In response to the increased pressure on the drug delivery device and the site of the body, interstitial fluid may build up within a part of the fluid delivery path of the pump which may cause a back pressure into the cannula (or even further up the fluid delivery path toward the reservoir and pump). As a result, the pump has to work harder to expel both the built-up interstitial fluid and the predetermined amount of insulin.

As a third example, the needle insertion component is operable to puncture the skin of the user with the needle to a depth of the subcutaneous region of the user's skin. The needle is hollow and within the needle is the flexible cannula. The needle insertion component is further operable to retract the needle from the user's skin and leave the flexible cannula within the skin to allow delivery of insulin. However, when the needle is inserted in the skin, the needle may leave punctured tissue below the open end of cannula from which insulin is output to the user's subcutaneous region. The punctured tissue allows the end of the cannula to freely move up and down and not be occluded. However, external pressure to the skin in the area of the drug delivery device may inadvertently push the cannula against the non-punctured skin around or below the open end of the cannula. As a result, the cannula may be forced into contact with the non-punctured skin around or below the cannula which may occlude the cannula. Alternatively, or in addition, the punctured skin may heal around the cannula and seal the cannula, thereby causing the occlusion.

In a fourth example, the body's immune system may attack the location of the needle insertion (i.e., insulin infusion site). The human body's immune response causes inflammation in the area around the cannula within the body and scar tissue may form, which causes an occlusion around the cannula and an occlusion of the pump.

Occlusions may also occur when insulin is not absorbed quickly enough by the subcutaneous tissues of the user. The delay in absorption may be related to a number of issues, such as the buildup of scar tissue if the pump is placed at a frequently used location on the user's body. Pump occlusion may be caused by different conditions. Any method or device operable to mitigate the occurrence of a pump occlusion is an improvement of the presently available wearable drug delivery systems.

FIG. 1 illustrates an example of a process for mitigating the potential causes of pump occlusion. The process 100 may be implemented by a controller coupled to a pump mechanism. For example, the controller may be operable to receive a control instruction to deliver a dosage of insulin (110). In response to the received control instruction, the controller may be operable to modify a pump rate for delivery of the dosage by at least adding additional time to a preset time period for delivering the dosage of insulin (120). A pump rate may be a rate at which a pump on a wearable drug delivery device is operable to deliver insulin to a user. The controller may be further operable to output an actuation command to actuate a pump to output the dosage of insulin included in the control instruction at the modified pump rate (130).

Figure 2A:
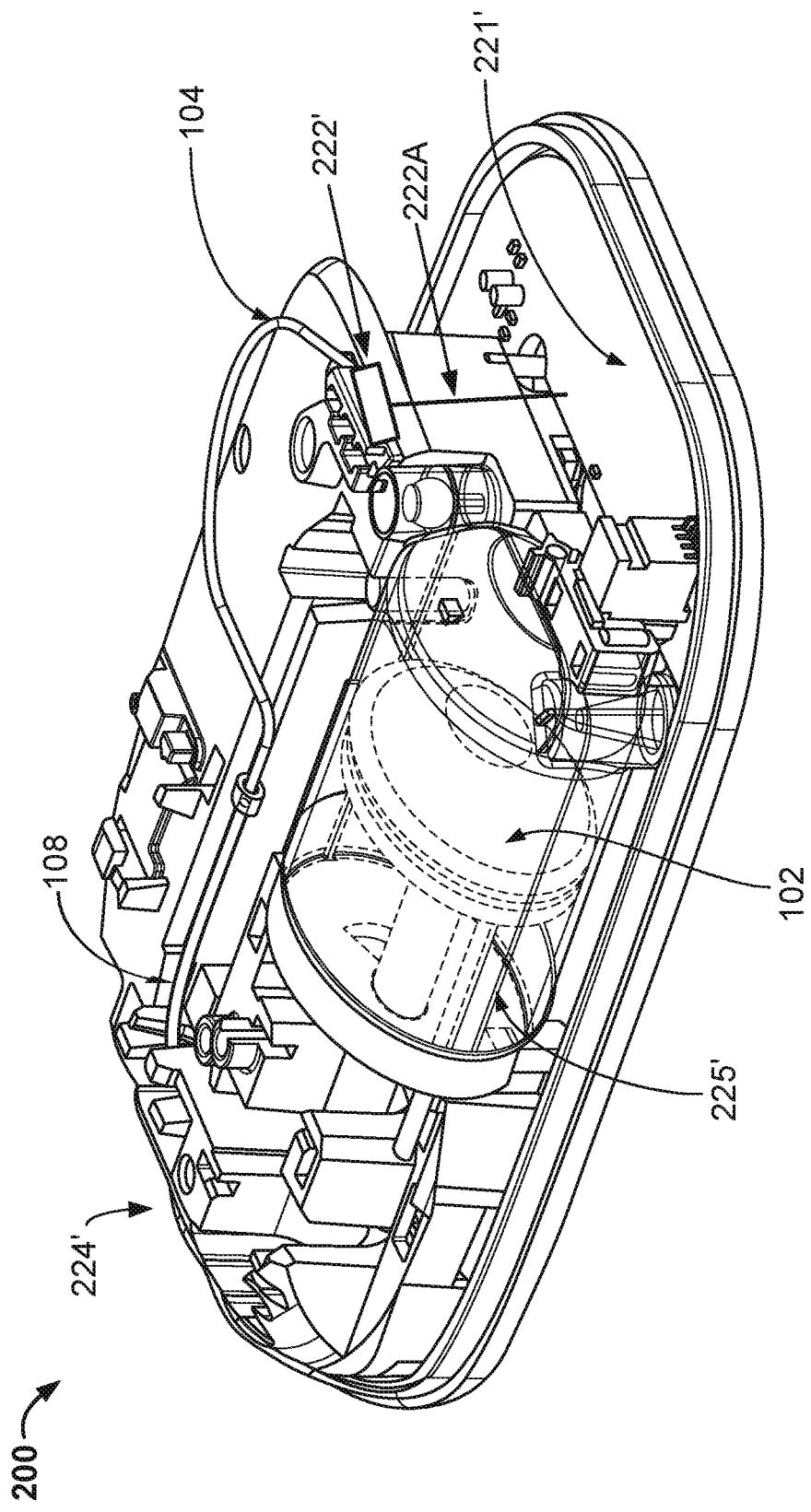
FIG. 2A illustrates an example of a drug delivery system suitable for implementing the example processes and techniques described herein.

An example of a medical device operable to implement the process 100 is shown in FIGS. 2 and 2A. The medical device 202 may include a controller 221, a pressure sensor 222, a memory 223, an AP application 229 and delivery control application 299 stored in the memory 223, a pump mechanism 224, a communication device 226, user interface 227, and a power source 228. a memory 223 may be operable to store programming code and applications including a delivery control application 299, an AP application 229 and data. The delivery control application 299 and an AP application 229 may optionally be stored on other devices, as shown in another examples.

The controller 221 may be coupled to the pump mechanism 224 and the memory 223. The controller 221 may include logic circuits, a clock, a counter or timer as well as other processing circuitry, and be operable to execute programming code and the applications stored in the memory 223 including the delivery control application. A communication device 226 may be communicatively coupled to the controller 221 and may be operable to wirelessly communicate with an external device, such as personal diabetes management device, a smart device (both shown in a system example), or the like.

The pressure sensor 222' may be a mechanical, electronic, or electromechanical sensor that is operable to measure changes in pressure of a fluid delivery path between the reservoir 225 and a cannula (not shown in this example) inserted into a user.

The pump mechanism may be operable to deliver a drug, like insulin, at a fixed rate. Typically, pump mechanisms are commanded by the controller 221 to deliver insulin at the fixed rate. For example, a fixed rate for the pump mechanism 224 may be a rate of approximately 0.05 Units per 2 seconds, or 0.025 per second, or 6 Units per 5 minutes, where insulin is measured in Units. These mechanical rates are different from physiological dosage rates that may be determined for a patient. For example, an AP application or AID algorithm executing on a personal diabetes management device or a smart phone may determine that a user's total daily insulin is 24 units per 24 hours, which may translate to an exemplary physiological dosage rate of 1 unit per hour that may be determined according to a diabetes treatment plan. However, the pump mechanism 224 may be operable to deliver insulin at rates different from the example physiological dosage rate of 1 unit per hour. Depending upon which dosage rate (e.g., either the example physiological dosage rate or the example mechanical rate of the pump mechanism), additional and different control algorithms may be implemented or applied to enable delivery of an appropriate insulin dosage by the pump mechanism 224. In an example, the medical device 202 may be attached to the body of a user, such as a patient or diabetic via, for example, an adhesive, and may deliver any therapeutic agent, including any drug or medicine, such as insulin, morphine, or the like, to the user. The medical device 202 may, for example, be a wearable device worn by the user. For example, the medical device 202 may be directly coupled to a user (e.g., directly attached to the skin of the user via an adhesive or the like). In an example, a surface of the medical device 202 may include an adhesive (not shown) to facilitate attachment to a user.

In various examples, the medical device 202 may be an automatic, wearable drug delivery device. For example, the medical device 202 may include a reservoir 225 configured to hold a liquid drug (such as insulin), a needle or cannula 233 (not shown) for delivering the drug into the body of the user (which may be done subcutaneously, intraperitoneally, or intravenously), and a pump mechanism (mech.) 224, or other drive mechanism, for transferring the drug from the reservoir 225, through a needle or cannula 233, and into the user.

The pump mechanism 224 may be fluidly coupled to reservoir 225, and communicatively coupled to the medical device controller 221. The pump mechanism 224 may be coupled to the reservoir 225 and operable to output the liquid drug from the reservoir 225 via a fluid delivery path and out of the cannula (shown in the example of FIG. 2A). The pump mechanism 224 may have mechanical parameters and specifications, such as a pump resolution, that indicate mechanical capabilities of the pump mechanism. The pump resolution is a fixed amount of insulin the pump mechanism 224 delivers in a pump mechanism pulse, which is an actuation of the pump mechanism for a preset time period. Actuation may be when power from the power source 228 is applied to the pump mechanism 224 and the pump mechanism 224 operates to pump a fixed amount of insulin in a preset amount of time from the reservoir 225.

The cannula 233 of FIG. 2 may be coupled to the reservoir 225 via a fluid delivery path 234 (and shown in the example of FIG. 2A). The cannula 233 may be operable to output the liquid drug to a user when the cannula 233 is inserted in the user.

The medical device 202 may also include a power source 228, such as a battery, a piezoelectric device, or the like, that is operable to supply electrical power to the pump mechanism 224 and/or other components (such as the controller 221, memory 223, and the communication device 226) of the medical device 202.

As shown in FIG. 2A, the drug delivery device 200 may include a plunger 102 positioned within the reservoir 225'. An end portion or stem of the plunger 102 can extend outside of the reservoir 225'. The pump mechanism shown generally as 224' may, under control of the controller 221', be operable to cause the plunger 102 to expel the fluid, such as a liquid drug (not shown) from the reservoir 225' and into the fluid component 104 and cannula 108 by advancing into the reservoir 225'. In various examples, the pressure sensor 222' may be integrated anywhere along the overall fluid delivery path of the drug delivery device 200, which includes the reservoir 225', a fluid delivery path component 104, the cannula 108) that is at the same approximate pressure as the outlet into the patient. An intervening membrane (not shown in FIG. 2A for simplicity) can be used to isolate the pressure sensor 222' from the fluid within the reservoir 225', the fluid delivery path component 104, and/or the cannula 108. Alternatively, a pliable gel or sufficiently soft rubber can be used to isolate the pressure sensor 222' from the fluid. In an example, the pressure sensor 222' may be integrated into the reservoir 225'.

In various embodiments, the pressure sensor 222' can have a round body to simplify sealing against the reservoir 102, the fluid delivery path component 104 and the cannula 108. In various embodiments, an integral lip seal can be used to seal the interface between the body of the pressure sensor 222' and the reservoir 225', the fluid delivery path component 104, and the cannula 108.

The pressure sensor 222' may be coupled to a controller 221' via connection 22A. The pressure sensor 222' can measure the absolute pressure of the reservoir 102 and/or the fluid delivery path component 104 (e.g., the overall fluid delivery path of the drug delivery device 200) and can provide an output signal to the controller 221'. In various embodiments, the pressure sensor 222' can take continuous readings of the absolute pressure. The output signal from the pressure sensor 222' can indicate the measured or detected absolute pressure and/or any other measured, detected, or derived pressure value.

The controller 221' can process the received signal from the pressure sensor 222'. The controller 221' may be implemented in hardware, software, or any combination thereof. In various examples, the controller 221' can be implemented as dedicated hardware (e.g., as an application specific integrated circuit (ASIC)). The controller 221' may be a constituent part of the drug delivery device 200, can be implemented in software as a computational model, or can be implemented external to the drug delivery device 200 (e.g., remotely).

The pressure sensor 222' can be an absolute pressure sensor that can detect both ambient pressure (e.g., absolute or atmospheric pressure) and relative pressure (e.g., gage or pumping pressure) introduced as the drug delivery device 200 displaces fluid (e.g., the fluid stored in the reservoir 225') in the overall fluid delivery path of the drug delivery device (e.g., including the reservoir 102 the fluid delivery path component 104 and the cannula 108). By using an absolute pressure sensor as the pressure sensor 222', it may also be possible to measure the effects of external ambient pressure on air within the reservoir 102.

In an example, the pressure sensor 222' may be operable to respond to pressure changes in the fluid delivery path and cause a signal to be provided to the controller 221'. The pressure sensor 222' may, for example, be one or more sensors positioned along the fluid delivery path that are operable to respond to changes in pressure of the fluid within the fluid delivery path. In a specific example, the pressure sensor may be an electromechanical sensor that includes a transducer. The transducer may be positioned to detect pressure within the fluid delivery path, for example, adjacent to a wall of the fluid delivery path or the like. In response to fluid being output from the reservoir, the walls of the fluid delivery path may become more rigid due to the increased pressure of the dispensed fluid. In response to the increased pressure caused by the dispensed fluid, which may cause the transducer positioned adjacent to a fluid delivery path wall to generate an electrical signal in response to an increased pressure. As the fluid in the dosage is delivered to the user, the increased pressure in the fluid delivery path of the reservoir 225' to the cannula 108 may cause the pressure sensor 222' to generate an output signal indicative of the pressure in the fluid delivery path.

The controller 221', for example, may be operable to determine an increase in a delivery pressure value when outputting insulin in comparison to a respective delivery pressure value associated with a respective earlier output of insulin. In another example, the controller may be operable to measure pressure by using the time it takes for the pump mechanism to push a specified amount of insulin (e.g., 0.1 Units) out of the reservoir. If the delivery of the specified amount of insulin takes longer than a threshold, the controller may cause a first alarm to notify the user of a possible problem with the pump. For example, even though, a pump resolution is 0.05 Units per 2 seconds, if there is a pump occlusion back pressure into the reservoir may cause the pump to fail to deliver the amount of insulin designated in a control instruction, which may result in extra pulses of the pump mechanism. For example, for each pulse, the pump piston is moved so an amount of 0.05 U is displaced from the reservoir 225'. If there is occlusion, it may take longer than 2 seconds to complete the pulse, which means that, in this example, there is not a fractional pulse (i.e., a pulse less than two seconds or a delivery of less than 0.05 U. If the time to complete a tick exceeds some threshold (e.g., 5 seconds, 9 seconds, or the like) the controller 221' may give an occlusion alarm that may be delivered to a user interface of a smart phone or PDM. In a further example, the controller 221' may be operable to report back to the AP algorithm how many pulses were delivered.

In various examples, the output signal generated by the pressure sensor 222' can be a voltage signal, a current signal, and/or an electrical charge signal that may be provided to the controller 221' via a connection, such as 222A. In general, the output signal from the pressure sensor 222' can indicate a measured pressure. In various examples, the output signal generated by the pressure sensor 222' may be an analog or digital data signal output by, for example, an inter-integrated circuit (I2C), serial peripheral interface (SPI), or any other known or customized synchronous or asynchronous data communication stream. Further, the pressure sensor 222' and the controller 221' can communicate over any known signaling protocol or standard including any known wired or wireless communication or signaling protocol. In various examples, the signal generated by the pressure sensor 222' for output and delivery to the controller 221' may be compensated for various environmental conditions, such as altitude, humidity or temperature, to remove or mitigate any error due to environmental changes. In a specific example, the controller 221' may be operable to convert the output signal received from the pressure sensor 222' into an indication of absolute pressure (e.g., pounds per square inch absolute (psia)) or the like. The controller 221' may be operable to process the output signal received from the pressure sensor 222' to determine whether a modification of the pump rate of the pump mechanism 224 is necessary, and, if determined to be necessary, may make the appropriate pump modification or modifications.

Figure 3A:
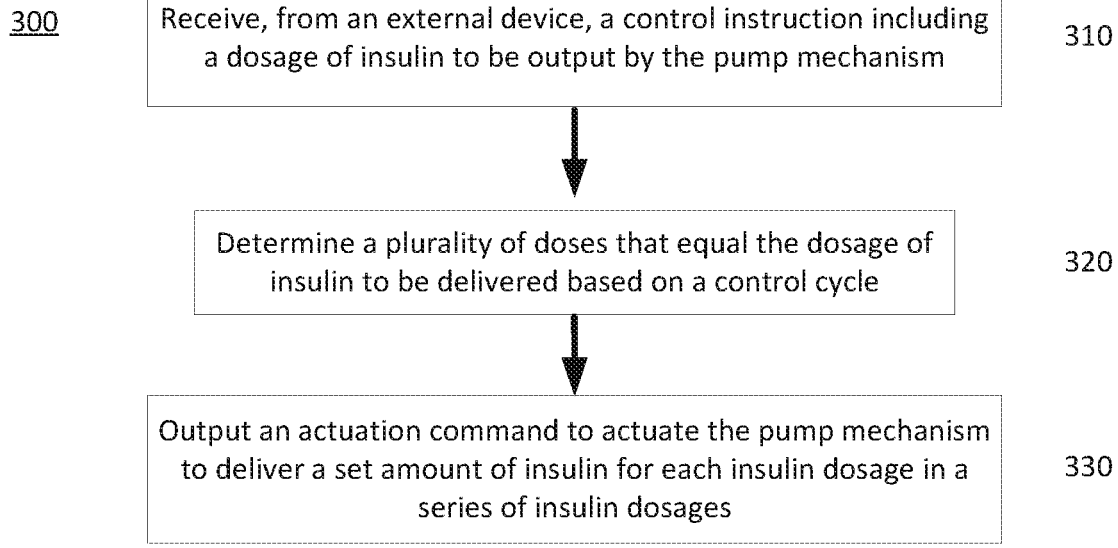
FIG. 3A illustrates an example of a process for determining a series of insulin dosages to be output over a control cycle.

An operational example may be helpful to further explain the pump rate and the determination of delivering a dosage of insulin over a period of time. FIG. 3A illustrates an example of a process for determining a series of insulin dosages to be output over a control cycle.

A control cycle may be a time period during which an AP application or an AID algorithm may process received data and information, such as a blood glucose measurement value provided by a continuous blood glucose measurement sensor or other devices, services, such as a cloud service, or the like. The duration of the control cycle may vary between different brands of AP applications and different sensors coupled to the respective AP applications. In the present example, a blood glucose sensor may periodically output a blood glucose measurement value. Upon receipt of each periodic blood glucose measurement value, an AP application may process the received blood glucose measurement value and generate a control instruction.

The control cycle may be the time from when an AP application receives a blood glucose measurement value and an immediately subsequent blood glucose measurement value. In the present examples, the control cycle is approximately 5 minutes.

For example, the process 300 is an algorithm for determining a series of insulin dosages to be output over a control cycle may be performed either by a personal diabetes management device (PDM) or by a medical device that delivers insulin to a user. In the process 300, a control instruction may be received that includes a dosage of insulin to be output by the pump mechanism. For example, an AP application or AID algorithm may determine that a bolus dosage is required to be delivered or has been requested by a user to be delivered. In response, the AP application or AID algorithm may generate a control instruction for output to a medical device that is operable to deliver insulin to the user.

In an operation that does not account for the possibility of a pump occlusion, the medical device may deliver the requested or required bolus of insulin as rapidly as possible given the pump resolution of the pump mechanism. In order to provide the requested or required bolus rapidly during the operation that does not account for the possibility of a pump occlusion, the AP application may output a series of control instructions that cause medical device to actuate the pump mechanism without pausing between actuations until the entire amount of insulin indicated in the control instruction is output from the reservoir.

In contrast to the operation that does not account for the possibility of a pump occlusion, the present examples account for the possibility of a pump occlusion. As in the example of FIG. 1 and the following examples, a controller of a medical device may be operable to modify a pump rate for delivery of the dosage of insulin provided using different techniques. As discussed with reference to the example medical device of FIG. 2, a delivery control application may be executed by a controller of the medical device.

In an example, a controller of the medical device may receive a control instruction from an AP application. The received control instruction may include a dosage of insulin to be delivered by the medical device. Instead of delivering the requested bolus of insulin in a rapid delivery without pausing between actuations until the entire amount of insulin indicated in the control instruction is delivered, the delivery control application executed by the controller of the medical device may be operable to deliver a number of microboluses continuously over the control cycle (e.g., 5 minutes). The following examples describe a pre-existing AID system that may utilize the devices, products, processes and techniques described herein to deliver its recommended dose of insulin every control cycle over a pre-defined period, such as the full control cycle, instead of attempting this delivery at a fixed pump rate without pausing to allow some absorption of the delivered insulin.

In more detail, an AID algorithm may recommend as a bolus insulin delivery ID(t). In response, a delivery control application executing on a medical device may be operable to, instead of delivering this ID(t) immediately, may deliver a portion of this delivery over an evenly distributed interval throughout its control cycle to minimize the buildup of pressure to thereby mitigate the rate of occlusion. The calculation of an evenly-distributed delivery amount of insulin over a control period may be described with reference to the following equations:

$$I_n(t) = \frac{I_D(t)}{R} \quad \text{Equation 1}$$

$$t_c(t) = \frac{t_i(t)}{I_D(t)/R} \quad \text{Equation 2}$$

In Equations 1 and 2, $I_D(t)$ is the algorithm's requested amount of insulin to be delivered for the current control cycle, R is the pump resolution that is an expression of an amount of insulin that is delivered by a pulse of the pump mechanism, $I_n(t)$ is the number of times the pump actuates every $t_i(t)$ time intervals to deliver insulin at the pump resolution R, where $t_c(t)$ is the time interval $t_i(t)$ divided by the number of pump actuations are needed to deliver an insulin delivery quantity (i.e., $I_D(t)/R$).

FIG. 3A illustrates an example of a process for determining a series of insulin dosages to be output over a control cycle of an automatic insulin delivery (AID) system.

In the example process 300 of FIG. 3A, a controller of the medical device may receive a control instruction including a dosage of insulin to be output by the pump mechanism (310) from an external device. An example of an external device may be a PDM, a smart phone, a smart wearable accessory, such as a smart watch, a fitness device, or the like, or some other type of computing device able to communicate with the medical device. The controller may evaluate the received control instruction to determine a dosage of insulin to be delivered over a control cycle of the AID system.

For example, an AID algorithm of the AID system may request a microbolus of 0.4 U (of insulin) at the beginning of a current control cycle. Briefly referring back to FIG. 2, the pump mechanism 224 of the medical device 202 as described with reference to the following examples may have a pump resolution of 0.05 Units of insulin that is delivered in 2 seconds, which means that in response to a control actuation command the pump mechanism delivers 0.05 Units of insulin over a time of 2 seconds. Of course, different pump resolutions are possible based on a type of electric motor, control mechanisms or logic used in the respective pump mechanism.

Figure 4:
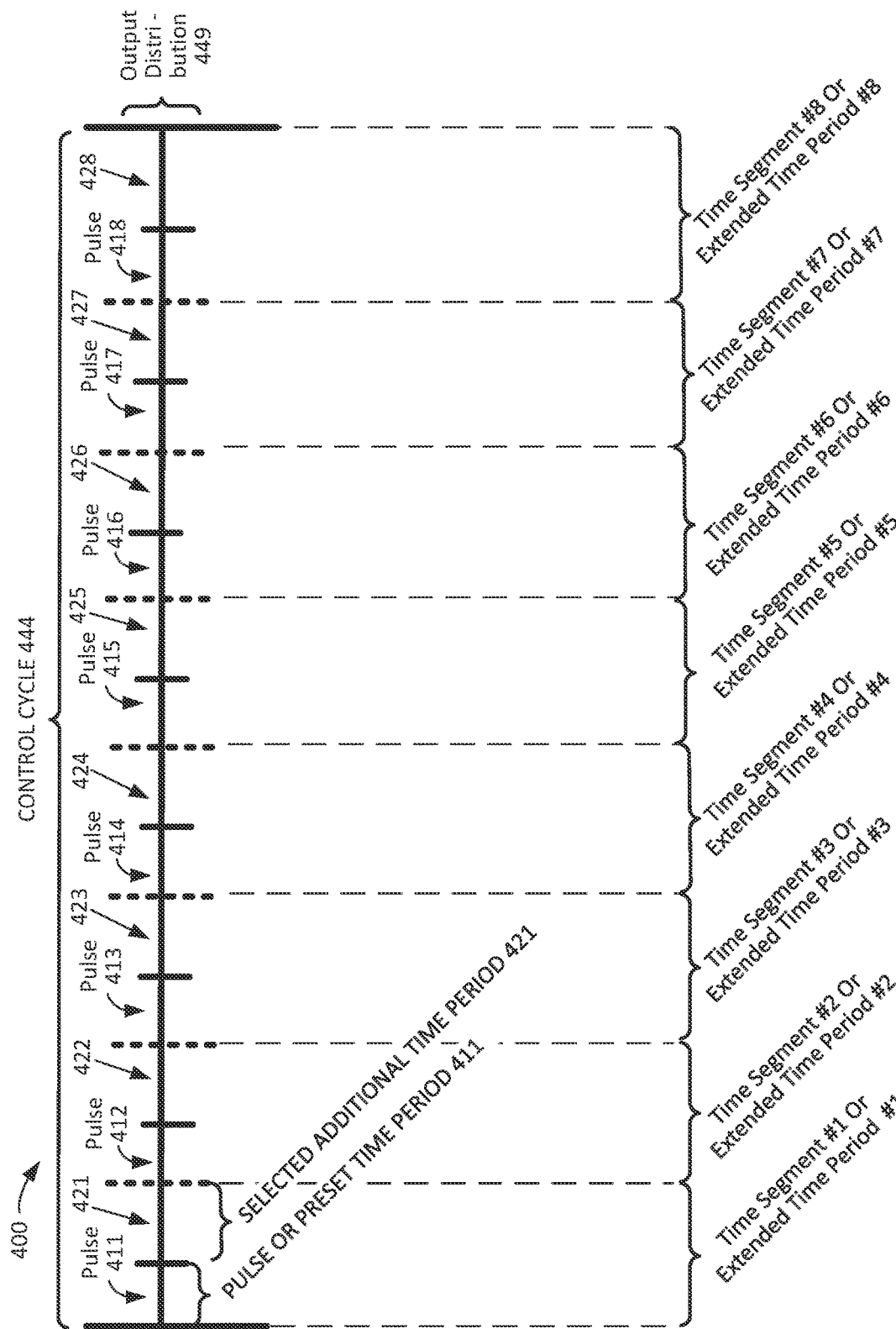
FIG. 4 shows a graphic illustrating time segmentation of a control cycle during the modification of a pump rate.

In the present example of FIG. 3A and FIG. 4, the 2 seconds of the pump resolution may be viewed as a preset time period and the 0.05 Units may be viewed as the minimum dosage that the pump mechanism may deliver in response to a control actuation command. In response to the control actuation command, the pump mechanism may "pulse" for 2 seconds during which the pump mechanism outputs the 0.05 Units of insulin. So, each pulse of the pump mechanism may be equated to either 0.05 Units of insulin or 2 seconds. may also be referred to the amount of insulin output by each pulse.

Returning to the example of FIG. 3A, when determining the dosage of insulin to be delivered, the controller may evaluate the dosage of insulin in the received control instruction with reference to the pump resolution and the time period of the control cycle. Based on the evaluation, the controller may determine a number of doses that equal the dosage of insulin to be delivered based on over a time period equal to the time of a control cycle (320). Once the dosage of insulin is determined by the controller, the controller may output an actuation command to the pump mechanism to deliver a set amount of insulin. The actuation command may actuate the pump mechanism to deliver a set amount of insulin for each insulin dosage in a series of insulin doses (330). Actuation of the pump mechanism is a pump mechanism pulse generated in response to the actuation command that causes the output of a drug from the reservoir.

Figure 3B:
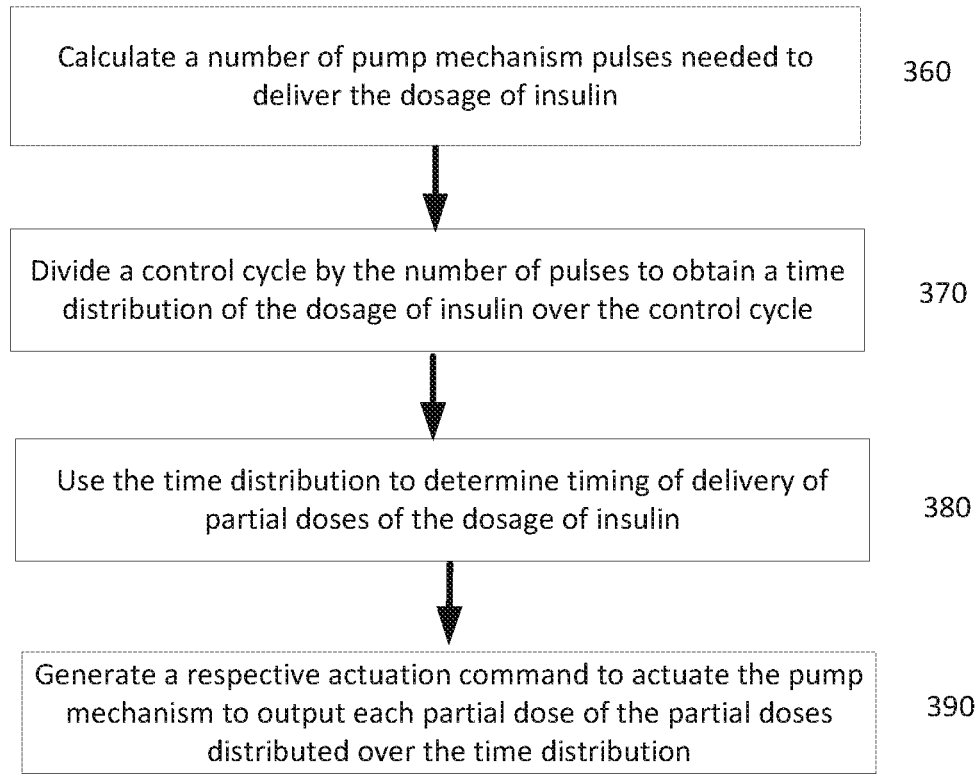
FIG. 3B illustrates an example of a process for modifying a pump rate suitable for use in the device examples of FIGS. 2 and 2A.

It may be helpful to describe an example of a process performed by the controller when evaluating dosage of insulin in the received control instruction with reference to the pump resolution and the time period of the control cycle. The process 303 of FIG. 3B is described with reference to FIG. 4 for more easily illustrating and explaining the process 303 as well as other processes that may be utilized. In the operational example of FIG. 3B, the control instruction from the external device may include a dosage of insulin equal to 0.4 Units of insulin.

In the example of the evaluation by the controller in response to the control instruction, the controller may process the dosage of insulin in the control instruction. FIG. 3B illustrates an example of a process for modifying a pump rate that may be implemented by the device shown in the examples of FIGS. 2 and 2A. FIG. 4 shows a graphic illustrating segmentation of a control cycle during the modification of a pump rate. This graphic may be helpful in understanding the process 303 described in FIG. 3B.

The evaluation process 303 of FIG. 3B includes the controller calculating a number of pump mechanism pulses need to deliver the dosage of insulin (360). Since the pump mechanism has a pump resolution in which a fixed amount of insulin (e.g., 0.05 U) is output over a preset time period (e.g., 2 seconds) during each pulse of the pump mechanism, the controller may determine a number of pulses of the pump mechanism needed to output the dosage of insulin included in the control instruction by, for example, dividing the 0.4 U (from the control instruction) by the 0.05 U. In the example, the number of pump mechanism pulses needed to deliver the dosage of insulin is (0.4/0.05=) 8. When a remainder of insulin is determined to be undelivered during a preset time period by a controller (such as controller 221'), the controller may be operable to accumulate (or carry over) the determined remainder of insulin to a next time period. In which case, the amounts of insulin to be delivered may not be evenly distributed across the respective time segments. The controller may be operable to either deliver the accumulated remainder of insulin and the scheduled insulin delivery during the next time segment or to revise the distribution so that the accumulated remainder is distributed with the scheduled delivery amounts over the remaining time segments. A revised distribution to include the accumulated remainder may be determined by summing the accumulated remainder and the total amount of insulin to be delivered over the remaining time segments and dividing the sum total by the remaining time segments.

In the example graphic 400 of FIG. 4, the control cycle 444 is shown as extending over 8 time segments or extended time periods (i.e. time segment #1-time segment #8 or extended time period #1-#8). Each of the time segments #1-#8 are further divided into 2 additional time segments. As shown, time segment #1 includes pulse 411 and a selected additional time period 421. The pulse 411 may be equal to the pump resolution or a preset time period. The pump resolution, or the resolution of the pump mechanism, may be an amount or volume of insulin that the pump mechanism delivers upon each actuation. Note the pump resolution may also be referred to as the pump mechanism resolution, the resolution of the pump, or resolution of the pump mechanism and the terms may be used interchangeably. The preset time period 411 may be equal to the period of time that the pump mechanism of the medical device takes to output the volume of fluid (i.e., the pump resolution), such as pump mechanism 224 of the medical device 202 of FIG. 2, outputs in response to a control actuation command.

The controller may be operable to divide the dosage of insulin by a resolution of the pump mechanism to produce the number of times the pump needs to actuate to output the insulin dosages as shown by the respective time segments in the example graphic 400 of FIG. 4. For example, the pump mechanism 224 of the medical device 202 as may be assumed to have a pump resolution of 0.05 Units of insulin that is delivered in 2 seconds, which means that in response to a control actuation command, a pulse of the pump mechanism delivers 0.05 Units of insulin over a time of 2 seconds. The pulse of the pump mechanism may be complete at the end of 2 seconds if no resistance is encountered (such as back pressure from an occlusion or the like). In the case of resistance, the pulse may last longer than 2 seconds due to a mechanical travel limit on the pump mechanism. The 2 seconds may be equal to the preset time period 411 in FIG. 4 and the 0.05 Units may be viewed as the fixed dosage that the pump mechanism may deliver in response to a control actuation command during the preset time period. The mechanical limit may be based on the travel of a ratchet gear (not shown) as the ratchet gear moves from one gear tooth to another, from one notch to another between gear teeth, or the like. In an example, the fastest time that the ratchet gear can move moves from one gear tooth to another, from one notch to another between gear teeth, or the like may be 2 seconds. The movement in the presence of an occlusion or back pressure may be 5 seconds, 9 seconds or the like.

As shown in FIG. 4, each time segment #1-#8 is formed by a preset time period or pulse 411, and a selected additional time period, such as 421. The pulse or preset time period 411 is equal to 2 seconds which is the time that the pump mechanism takes to output a dose of insulin equal to 0.05 Units. Each pulse 411-418 has a fixed time period that is equal to the time period of the pump resolution. The selected additional time period 421 is an amount of time that the controller has calculated to wait until issuing a subsequent actuation command. The selected additional time periods 421-428 may be of equal duration to allow sufficient absorption of the outputted insulin. In the example of FIG. 4, each of the time segments #1-#8 is of equal duration.

At 370, the controller may be operable to calculate an output distribution of the dosage of insulin by the pump mechanism by dividing a duration of a control cycle by the number of pump mechanism pulses to obtain an output distribution, such as output distribution 449 of FIG. 4. The output distribution 449 may be, for example, a series of discrete time segments distributed over the duration of control cycle 444 and during which a partial insulin dose is output by the pump mechanism. Alternatively, the output distribution 449 may be a series of partial doses of insulin dosages output at discrete times distributed over the control cycle 444. The output distribution 449 illustrates the distributed output of the dosage of insulin indicated in the control instruction as partial doses of insulin distributed over the control cycle 444 of FIG. 4. The output distribution 449 may be used by the controller to determine timing of delivery of the partial doses of the dosage of insulin. For example, each pulse 411-418 may output of a dose of insulin that is an of the dosage of insulin indicated in the control instruction.

In addition to determining the output distribution, the controller also determines the timing of the partial doses of the dosage of insulin (380). For example, the timing of the partial doses of the dosage of insulin may be represented by the selected additional time periods 421-428. Each additional time period 421-428 is a period of time that serves as a delay or a waiting period after completion of a corresponding pulse 411-418.

Keeping with the example dosage of insulin in the control instruction being 0.4 Units, the controller upon determining the number of pump mechanism pulses needed to deliver the 0.4 Units is 8 may divide the duration of the control cycle 444 by 8 to determine the duration of each time segment #1-8. As mentioned, a control cycle such as 444 may be 5 minutes or 300 seconds (5×60 seconds) in duration. The duration of each time segment #1-#8, in this example, may be equal to the time period of the control cycle in seconds (i.e., 300) divided by the number of pump mechanism pulses (i.e., 8). In this example, the duration of each time segment #1-#8 may be equal to 37.5 seconds.

Based on this determination the controller generate a respective actuation command to actuate the pump mechanism to output each partial dose of the partial doses distributed over the output distribution (390). For example, the controller may generate a respective actuation command that corresponds to pulse 411 of time segment #1, and at after the 37.5 seconds allocated to time segment #1, the controller may generate another respective actuation command that corresponds to pulse 412 of time segment #2. A timer within the controller may be reset or may indicate a start of time segment #2. The respective generation of subsequent actuation commands for time segment #3, time segment #4, time segment #5, time segment #6, time segment #7 and time segment #8 may be performed until the control cycle 444 is completed. By the completion of time segment #8 and the corresponding completion of the control cycle 444, the 0.4 Units of insulin in the dosage of insulin included in the control instruction is output by the pump mechanism.

Recall that under an operation that does not pause to account for pump occlusions, the controller may generate actuation signals that cause the delivery of the instructed 0.4 Units immediately without any pauses at the pump resolution. In such an operation that does not account for pump occlusions, the controller may generate actuation signals every 2 seconds at the start of a control cycle, the pump mechanism may need to receive 8 actuation signals to deliver the instructed 0.4 Units within 16 seconds (i.e., 2 seconds times the 8 actuation signals). The control cycle 444 may be as long as 5 minutes and the 16 second delivery of insulin may be less than the total time duration of time segment #1.

It is also possible for the controller to take different approaches to determining the output distribution 449 and the time segments #1-#8.

For example, the controller may be operable to determine a number of times the pump mechanism needs to actuate to output the dosage of insulin included in the control instruction (e.g., 8). Using the determined number of times the pump mechanism needs to actuate to output the dosage of insulin, the controller may segment the control cycle 444 into time segments #1-#8 by dividing a duration of the control cycle 44 by the determined number of times the pump mechanism ought to actuate. The segmentation of the 300 seconds of the control cycle 444 provides eight time segments #1-#8 of 37.5 seconds. As noted, each time segment #1-#8 may include a pump resolution or preset time period and a respective additional time period 421

In the operational example of FIG. 3B at 380, each time segment #1-#8 is 37.5 seconds in duration. The controller is operable to generate a respective actuation command that actuates the pump mechanism for each time segment #1-#8. As shown in FIG. 4, the pump mechanism pulses 411-418 occur at the start of each respective time segment #1-#8. Each pump mechanism pulse, such as pulse 411 of time segment #1, pumps 0.05 Units of insulin for 2 seconds and stops, the controller delays the generation of an actuation command for application at the start of time segment #2 for 35.5 seconds (i.e., 37.5 seconds minus 2 seconds). The 35.5 seconds may be measured by a clock, a counter or timer accessible by or within the controller. The 35.5 seconds may be the selected additional time period 421. An advantage of the selected additional time period 421 is that this delay enables the partial dose of insulin to be absorbed within the user and thereby mitigate the effects of any pump occlusion.

In the example of FIGS. 3B and 4, after the passing of the selected additional time period (e.g., the delay), the controller causes the actuation of the pump mechanism, which pulses at 412 to output another 0.05 Units of insulin. Since the pump mechanism does not have the ability to gradually deliver 0.05 U, the pump outputs 0.05 Units over the 2 seconds of the preset time period or pulse, then pauses for 35.5 seconds, then repeats. The processes of the examples of FIGS. 1, 3A and 3B enable spreading the 0.4 Units of insulin to be output over a time of the control cycle that is greater much more than the 16 seconds (i.e., 8 pulses to deliver 0.4 units×2 seconds per pulse) that would happen if the selected additional time period was not incorporated to enable absorption of a partial dose of insulin.

In a further example, the pump rate modification may be applied to other insulin deliveries than automated insulin deliveries. For example, user requested boluses can also be delivered at a lower than maximal rate. In the example, if a user requests a bolus of 3 Units, the delivery control application may be operable to cause this delivery can occur via several pump mechanism pulses (i.e., 6) that have a selected additional time period of, for example, 3 seconds between pulses. As a result, the 3 seconds may be combined with the 2 seconds of the pump resolution to provide a time segment of 5 seconds which delivers the requested bolus of 3 Units within 3 seconds to allow for a pump occlusion.

While the pulse in response to an output of the actuation command at a beginning of each respective time segment of the control cycle is shown in FIG. 4, the pulses 411-418 are shown as occurring at the beginning of each time segment #1-#8 in FIG. 4. Of course, the actuation command may be delivered at other times within the respective time segments so long as the selected additional time periods 421-428 are of sufficient time to allow for absorption of the insulin and mitigate the effects of any pump occlusion or other absorption problems after output of the dosage of insulin.

The foregoing processes used to modify the pump rate of the pump mechanism may be applied in response to a pump occlusion as well as other reasons including physiological reasons such as difficulty in absorption of a particular type of insulin or medication. However, a process for detecting the presence of a pump occlusion may be explained with reference to FIGS. 5A and 5B.

The following examples may be useful when absorption of the insulin is occurring at a rate that is less than optimum or is occurring due to factors, such as pump occlusion or the like. As discussed above, pump occlusions may occur for a number of reasons. It may be helpful to describe examples of processes and techniques for determining the presence of a pump occlusion with reference to FIGS. 5A and 5B.

FIG. 5A illustrates an example of a process for detecting a pump occlusion that may result in a modification of a pump rate.

In the process 500, a controller of a medical device may be operable to receive a pressure sensor signal from a pressure sensor in a fluid delivery path through which the dosage of insulin is delivered (510). The pressure sensor signal may include a pressure value. The controller may be further operable to determine whether the pressure value exceeds a pressure threshold (520). The pressure threshold, for example, may be equal to an amount of pressure that the pump mechanism experiences when outputting a drug when no form of pump occlusion is present, and the drug is substantially absorbed by bodily tissue at or near an output of a cannula or needle. This may be determined from testing prior to manufacturing of the pump mechanism, for example. The threshold may be stored in a memory of the medical device during manufacture, may be set (or updated) and stored after an initial use of the medical device, or the like.

At 530, in response to the determination that the pressure value exceeds the threshold, the controller may access a lookup table stored in the memory or may communicate with and external device for an additional time increment. In the lookup table example, the lookup table may contain a number of pressure values that exceed the pressure threshold with corresponding additional time increments. The additional time increments may select an additional time increment to be added to the preset time period of the pump mechanism. The controller may be operable to use the additional time increment in the modification of the pump rate (540). As explained in the examples of FIGS. 3A, 3B and 4, a preset time period is an amount of time it takes the pump mechanism to output the dosage of insulin after receipt of the actuation command. In step 540, for example, the controller may be operable to calculate the extended time period or time segment (as in the example of FIGS. 3A, 3B and 4) by adding the selected additional time increment to the preset time period to arrive at the time segment and the modified pump rate.

Alternatively, a process using a pressure to determine the presence of a pump occlusion may be implemented by the controller. FIG. 5B illustrates another example of a process for detecting a pump occlusion that may result in a modification of a pump rate.

The process 503 may be implemented by the execution of programming code by the controller of the pump mechanism in response to pressure sensor signals received from a pressure sensor that may be coupled to the pump mechanism and the controller. In the example of FIG. 5B, the controller may be operable to receive, at 563, a pressure sensor signal from the pressure sensor, which is coupled to a fluid delivery path of the pump mechanism through which the dosage of insulin is output.

At 573, the controller may calculate an amount of delivery back pressure based on the received pressure sensor signal. For example, the controller may monitor the pressure sensor signal received from the pressure sensor at the beginning, during, and/or end of each pulse of the pump mechanism.

The controller may be operable to determine whether the calculated amount of delivery back pressure exceeds a threshold (583). The controller, for example, may use the respective pressure sensor signals to determine whether the pressure sensor signal is indicating increases in back pressure that are greater than an operation without a pump occlusion.

In the example, the controller, based on the result of the determination, may generate an indication that the deliver pressure value has increased (593). The programming code executed by the controller may, for example, in response the generated indication may perform pump rate modification processes, such as those discussed with reference to the examples of FIGS. 3A, 3B and 4.

The presence of the pressure sensor and the functions provided by delivery control application as described with reference to the earlier examples serves to reduce the buildup of back pressure and thus reduces the increased risk of occlusion that may be caused by a fixed rate of insulin delivery, which improves the safety of the AID system to the users.

Figure 6:
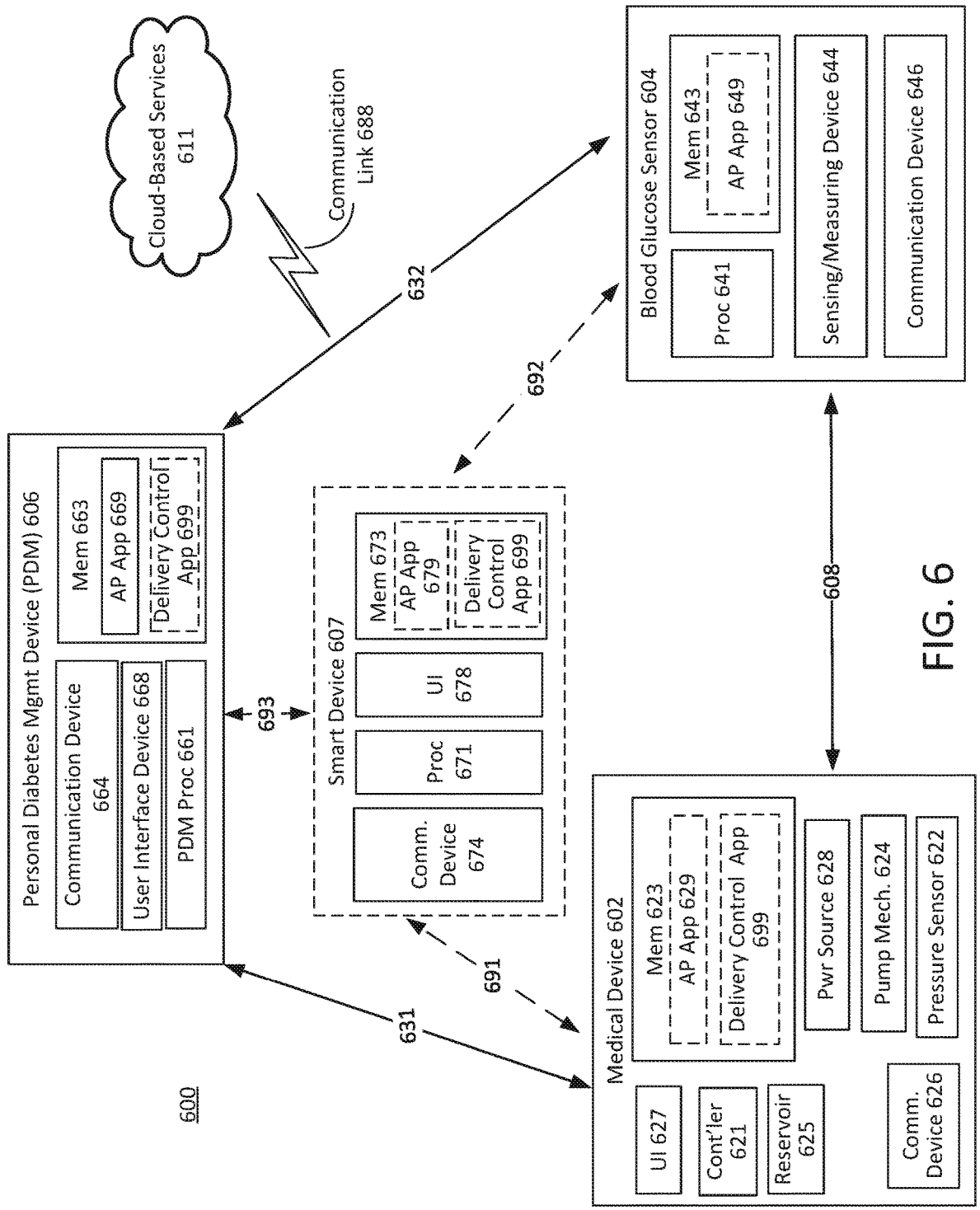
FIG. 6 illustrates an example of system suitable to implement the processes and techniques described herein.

FIG. 6 illustrates an example of system suitable to implement the processes and techniques described herein.

In the examples of FIGS. 1, 3A, 3B, 5A and 5B, the example processes may be implemented by programming code, such as a delivery control application, an AP application or automatic insulin deliver (AID) application, or a combination of applications that are executed by a processor. The AP application or the AID application when executed by a processor may utilize inputs and calculations as described with respect to the foregoing examples.

It may be helpful to discuss an example of a drug delivery system that may implement the process example of FIGS. 1, 3A, 3B, 5A and 5B. FIG. 6 illustrates an example of a drug delivery system suitable for implementing the example processes and techniques described herein including those described with reference to FIGS. 1, 3A, 3B, 5A and 5B. Details of an example of a medical device (such as 202 of FIG. 2 or 200 of FIG. 2A), a wearable drug delivery device, a "drug delivery device," such as an OmniPod® delivery device provided by Insulet Corp, or the like, are described with reference to the example system of FIG. 6.

The drug delivery system 600 may be an automatic drug delivery system that may include a medical device 602 (also referred to as "a drug delivery device", "a wearable drug delivery device," or "a drug delivery device"), a blood glucose sensor 604 (also referred to as "a continuous glucose monitor" or "a blood glucose measurement device"), and a personal diabetes management (PDM) device 606. The system 600, in an example, may also include a smart device 607, which may be operable to communicate with the PDM 606 and other components of system 600 either via a wired or wireless communication link, such as 691, 692 or 693. In a specific example, the smart device 607 is coupled to the PDM 606 only via a wireless communication link 693, which may be a wireless communication link that utilizes the Bluetooth communication protocol or the like.

The medical device 602 may include a controller 621, a pressure sensor 622, a memory 623, an AP application 629 and a delivery control application 699 stored in the memory 623, a pump mechanism 624, a communication device 626, user interface 627, and a power source 628. The pump mechanism may be operable to deliver a drug, like insulin, at fixed rate of the mech. Typically, pumps are commanded by a controller to deliver insulin at the fixed rate. For example, an ordinary rate for the pump mechanism 624 may be 0.05 Units per 2 seconds or 0.025 Units per second or 6 Units per 5 minutes, where insulin is measured in Units. These mechanical rates are different from physiological rates that may be determined for a patient. For example, the AP algorithm may determine that a user's total daily insulin is 24 Units per 24 hours, which may translate to a physiological rate of 1 unit per hour that may be determined according to a diabetes treatment plan. However, the pump mechanism may be operable to deliver insulin at rates greater than or less than 1 unit per hour. In an example, the medical device 602 may be attached to the body of a user, such as a patient or diabetic via, for example, an adhesive, and may deliver any therapeutic agent, including any drug or medicine, such as insulin, morphine or the like, to the user. The medical device 602 may, for example, be a wearable device worn by the user. For example, the medical device 602 may be directly coupled to a user (e.g., directly attached to a body part and/or skin of the user via an adhesive or the like). In an example, a surface of the medical device 602 may include an adhesive (not shown) to facilitate attachment to a user.

The medical device 602 may include a number of components to facilitate automatic delivery of a drug (also referred to as a therapeutic agent) to the user. The medical device 602 may be operable to store the drug (i.e., insulin) and to provide the drug to the user. The medical device 602 is often referred to as a pump, or an insulin pump, in reference to the operation of expelling insulin from the reservoir 625 for delivery to the user. While the examples refer to the reservoir 625 storing insulin, the reservoir 625 may be operable to store other drugs or therapeutic agents, such as morphine or the like, that are suitable for automatic delivery.

In various examples, the medical device 602 may be an automatic, wearable drug delivery device. For example, the medical device 602 may include a reservoir 625 for storing the drug (such as insulin), a needle or cannula (not shown) for delivering the drug into the body of the user (which may be done subcutaneously, intraperitoneally, or intravenously), and a pump mechanism (mech.) 624, or other drive mechanism, for transferring the drug from the reservoir 625, through a needle or cannula (not shown), and into the user. The pump mechanism 624 may be fluidly coupled to reservoir 625, and communicatively coupled to the medical device controller 621. The medical device 602 may also include a power source 628, such as a battery, a piezoelectric device, or the like, for supplying electrical power to the pump mechanism 624 and/or other components (such as the controller 621, memory 623, and the communication device 626) of the medical device 602. Although not shown, an electrical power supply for supplying electrical power may similarly be included in each of the sensor 604, the smart device 607 and the PDM device 606.

The blood glucose sensor 604 may be a device communicatively coupled to the PDM processor 661 or controller 621 and may be operable to measure a blood glucose value at a predetermined time interval, such as every 5 minutes, or the like. The blood glucose sensor 604 may provide a number of blood glucose measurement values to the AP applications (e.g., 629, 649, 669, or 679) operating on the respective devices (e.g., 602, 604, 606, or 607). The AP applications 629, 649, 669 and 679 may be replaced with an AID algorithm that is also operable to control and communicate with connected devices, such as medical device 602 and sensor 604, and manage a personal diabetes treatment program, and provide the functions and services as described herein.

The medical device 602 may provide the insulin stored in reservoir 625 to the user based on information (e.g., blood glucose measurement values, predicted future blood glucose measurements, evaluations based on a user request for a bolus, pressure sensor signals received from the pressure sensor 622), and the other information provided by the sensor 604, smart device 607, and/or the management device (PDM) 606. For example, the medical device 602 may contain analog and/or digital circuitry that may be implemented as a controller 621 for controlling the delivery of the drug or therapeutic agent. The circuitry used to implement the controller 621 may include discrete, specialized logic and/or components, an application-specific integrated circuit, a microcontroller or processor that executes software instructions, firmware, programming instructions or programming code (enabling, for example, the artificial pancreas application (AP App) 629 as well as the process examples of FIGS. 1, 3A, 3B, 5A and 5B) stored in memory 623, or any combination thereof. For example, the controller 621 may execute a control algorithm, such as the artificial pancreas application 629, and other programming code that may make the controller 621 operable to cause the pump to deliver doses of the drug or therapeutic agent to a user at predetermined intervals or as needed to bring blood glucose measurement values to a target blood glucose value. In an example, the AP application (App) 629 may include programming code that is operable upon execution by the controller 621 to provide the example processes for adjusting or modifying total daily insulin settings, or the like as described with reference to FIGS. 1, 3A, 3B, 5A and 5B. The user preferences for total daily insulin settings may be programmed, for example, into an artificial pancreas application 629 by the user or by a third party (such as a health care provider, medical device manufacturer, or the like) using a wired or wireless link, such as 631, between the medical device 602 and a personal diabetes management device 606 or other device, such as a computing device at a healthcare provider facility. In an example, the pump or medical device 602 is communicatively coupled to the PDM processor 661 of the personal diabetes management device via the wireless link 631 or via a wireless link, such as 691 from smart device 607 or 608 from the sensor 604. The pump mechanism 624 of the medical device 602 may be operable to receive an actuation signal from the PDM processor 661, and in response to receiving a command signal or an actuation signal, expel insulin from the reservoir 625 based on the commands from an AP application, such as 669.

The drug delivery system 600 may be operable to implement the process examples illustrated in FIGS. 1, 3A, 3B, 5A and 5B by executing a delivery control application in cooperation with an AP application. The delivery control application 699 or AP application 629 may be operable to receive a signal from the pressure sensor 622.

In an operational example, the AP application 669 executing in the personal diabetes management device 606 may be operable to control delivery of insulin to a user. For example, the AP application 669 may be operable to determine timing of an insulin dose and may output a command signal to the medical device 602 that actuates the pump mechanism 624 to deliver an insulin dose. In addition, the AP application (or AID algorithm) 669 when loaded with programmed code that provides instructions for the functionality of FIGS. 1, 3A, 3B, 5A and 5B.

In the operational example, the AP application or AID algorithm may have requested, via a command signal to the medical device 602, delivery of an insulin delivery dosage for a current cycle, say every 5 minutes, which is equal to the control cycle of the AP application or AID algorithm. The controller 621 of the medical device 602 may evaluate the requested insulin delivery using the delivery control application 699.

Continuing with the operational example, the delivery control application 699 may receive the requesting insulin delivery. For example, the requested insulin delivery dosage (referred to as ID(t)) may be equal to 0.4 Units of insulin as discussed above. In cases where a pump occlusion is not present, the controller 621 of the medical device 602 may actuate the pump mechanism 624 to deliver the ID(t) dosage immediately at the mechanical pump rate of 0.05 units every 2 seconds (which will deliver the 0.4 units of insulin in approximately 16 seconds). However, in an example, the pressure sensor signal received from the pressure sensor 622 may have indicated a degree of back pressure, which the deliver control application 699 may be operable to interpret as indicating a partial pump occlusion. The pressure sensor 622 may be operable to provide a signal to the controller 621 indicating the partial pump occlusion. The controller 621, in the presence of the indicated partial pump occlusion, may be operable to modify the delivery of the requested insulin delivery by modifying the mechanical pump rate of the pump mechanism 624. Alternatively, the controller 621 may automatically extend all requested insulin deliveries over the control cycle regardless of whether there is a pump occlusion or not.

In the presence of the partial pump occlusion, the controller 621 may modify the delivery of insulin by extending a time interval to deliver the requested insulin delivery (ID(t)) amount. For example, the controller 621 may be operable to extend the time interval to fit the control cycle or control cycle, such as 5 minutes, 10 minutes or the like, of the AP application or AID algorithm. Using a 5 minute control cycle and the ID(t) amount as 0.4 Units in an example in which the controller receives a signal from the pressure sensor 622 indicating a pump occlusion, the controller 621 may determine a pump rate modification is needed. As a result, instead of the pump delivering the 0.4 U in the 16 seconds that corresponds to a typical drug delivery, the controller modifies the delivery and extends the delivery over the 5 minutes (or 300 seconds (5 minutes×60 seconds/minute)) of the control cycle. For example, the controller may divide the 300 seconds of the control cycle by the number of pump resolution cycles for delivering the 0.4 U of insulin. In this example the number of pump resolution cycles is equal to 8 (i.e., 0.4 Units divided by the pump resolution of 0.05 U) which equals 37.5 seconds (i.e., 300 seconds/8=37.5).

Based on this calculation made by the controller 621, the controller 621 may actuate the pump mechanism 624 to deliver 0.05 U of insulin every 37.5 seconds for the 300 seconds (i.e., the 5 minute control cycle) after which substantially all of the entire amount of the requested insulin delivery ID(t) is output by the pump mechanism 624.

By extending the time interval, the controller may be able to overcome, or at least mitigate, the effects of the pump occlusion. For example, if the pump occlusion is caused by a slow absorption rate of the insulin due to a buildup of scar tissue in or around the infusion site, the slower rate of delivery over the extended time period may enable the insulin to be absorbed in or around the infusion site.

Bolus dosages may be handled in a similar manner by the medical device 602. For example, in response to a meal or other event that may cause an increase in blood glucose, a user may request a bolus dosage of insulin. In a hypothetical example, the user may request the delivery of 3 Units of insulin as the bolus dosage. In response to an input by the user or a generated request by the AP application or AID algorithm, the AP application or AID algorithm in the PDM 606 or the like may deliver a control signal to the medical device 602 indicated that a bolus delivery of 3 units is requested. The controller 621 may receive and interpret the control signal to instruct the pump mechanism 624 to deliver a requested insulin delivery (ID(t)) amount of 3 U. In response to the control signal, the controller may divide the ID(t) amount by the pump resolution (e.g., 3 U/0.05) to determine a number of pulses (e.g., 3 U/0.05=60) that the pump mechanism would need to generate to deliver the requested insulin delivery (ID(t)) amount. Without a pump occlusion and the pump operating at the pump resolution of 0.05 U per 2 seconds, the pump mechanism 624 may deliver the ID(t) of 3 U within 120 seconds or 2 minutes (i.e., 60 times 2 seconds). However, if a partial pump occlusion is detected by the pressure sensor 622, the controller 621 may extend the time interval for delivery of the ID(t). For example, the time for the control cycle may be 5 minutes, the controller may determine the number of seconds in the control cycle (5 minutes time 60 seconds/minute=300 seconds). The 300 seconds is divided by the number of pulses (60) so 5 seconds is the time for the pump to deliver 0.05 U of insulin. In other words, the controller 621 commands the pump mechanism 624 to deliver the 0.05 U of insulin over a 5 second period instead of the 2 seconds.

The other devices in the system 600, such as personal diabetes management device 606, smart device 607 and sensor 604, may also be operable to perform various functions including controlling the medical device 602. For example, the personal diabetes management device 606 may include a communication device 664, a PDM processor 661, and a personal diabetes management device memory 663. The personal diabetes management device memory 663 may store an instance of the AP application 669 that includes programming code, that when executed by the PDM processor 661 provides the process examples described with reference to the examples of FIGS. 1, 3A, 3B, 5A and 5B. The personal diabetes management device memory 663 may also store programming code for providing the process examples described with reference to the examples of FIGS. 1, 3A, 3B, 5A and 5B.

The smart device 607 may be, for example, a smart phone, an Apple Watch®, another wearable smart device, including eyeglasses, provided by other manufacturers, a global positioning system-enabled wearable, a wearable fitness device, smart clothing, or the like. Similar to the personal diabetes management device 606, the smart device 607 may also be operable to perform various functions including controlling the medical device 602. For example, the smart device 607 may include a communication device 674, a processor 671, and a memory 673. The memory 673 may store an instance of the AP application 679 and/or an instance of an AID application (not shown) that includes programming code for providing the process examples described with reference to the examples of FIGS. 1, 3A, 3B, 5A and 5B. The memory 673 may also as store programming code and be operable to store data related to the AP application 679 or an instance of an AID application (not shown). In an operational example, the AP application 679 may be operable to provide functionality similar to or the same the functionality as described with reference to the instance of the AP application 669.

The sensor 604 of system 600 may be a continuous glucose monitor (CGM) as described above, that may include a processor 641, a memory 643, a sensing or measuring device 644, and a communication device 646. The memory 643 may, for example, store an instance of an AP application 649 as well as other programming code and be operable to store data related to the AP application 649 and process examples described with reference to FIGS. 1, 3A, 3B, 5A and 5B. The AP application 649 may also include programming code for providing the process examples described with reference to the examples of FIGS. 1, 3A, 3B, 5A and 5B.

Instructions for determining the delivery of the drug or therapeutic agent (e.g., as a bolus dosage) to the user (e.g., the size and/or timing of any doses of the drug or therapeutic agent) may originate locally by the medical device 602 or may originate remotely and be provided to the medical device 602. In an example of a local determination of drug or therapeutic agent delivery, programming instructions, such as an instance of the artificial pancreas application 629, stored in the memory 623 that is coupled to the medical device 602 may be used to make determinations by the medical device 602. In addition, the medical device 602 may be operable to communicate with the cloud-based services 611 via the communication device 626 and the communication link 688. In an example, the system 600 may include one or more components operable to implement the process examples of FIGS. 1, 3A, 3B, 5A and 5B.

Alternatively, the remote instructions may be provided to the medical device 602 over a wired or wireless link (such as 631) by the personal diabetes management device (PDM) 606, which has a PDM processor 661 that executes an instance of the artificial pancreas application 669, or the smart device 607 (via communication link 691), which has a processor 671 that executes an instance of the artificial pancreas application 669 as well as other programming code for controlling various devices, such as the medical device 602, smart device 607 and/or sensor 604. In an example, the send a message to a server, for example, in the cloud services 611 or the like, requesting downloading of the one or more cost functions to a personal diabetes management (PDM) 606 or smart device 607. The medical device 602 may execute any received instructions (originating internally or from the personal diabetes management device 606) for the delivery of the drug or therapeutic agent to the user. In this way, the delivery of the drug or therapeutic agent to a user may be automatic.

In various examples, the medical device 602 may communicate via a wireless link 631 with the personal diabetes management device 606. The personal diabetes management device 606 may be an electronic device such as, for example, a smart phone, a tablet, a dedicated diabetes therapy personal diabetes management device, or the like. The personal diabetes management device 606 may be a wearable wireless accessory device. The wireless communication links 608, 631, 632, 691, 692 and 693 may be any type of wireless link provided by any known wireless standard. As an example, the wireless communication links 608, 631, 632, 691, 692 and 693 may enable communications between the medical device 602, the personal diabetes management device 606 and sensor 604 based on, for example, Bluetooth®, Wi-Fi®, a near-field communication standard, a cellular standard, or any other wireless optical or radio-frequency protocol.

The sensor 604 may be a glucose sensor operable to measure blood glucose and output a blood glucose value or data that is representative of a blood glucose value. For example, the sensor 604 may be a glucose monitor or a continuous glucose monitor (CGM). The sensor 604 may include a processor 641, a memory 643, a sensing/measuring device 644, and communication device 646. The communication device 646 of sensor 604 may include one or more sensing elements, an electronic transmitter, receiver, and/or transceiver for communicating with the personal diabetes management device 606 over a wireless link 632 or with medical device 602 over the link 608. The sensing/measuring device 644 may include one or more sensing elements, such as a glucose measurement, heart rate monitor, or the like. The processor 641 may include discrete, specialized logic and/or components, an application-specific integrated circuit, a microcontroller or processor that executes software instructions, firmware, programming instructions stored in memory (such as memory 643), or any combination thereof. For example, the memory 643 may store an instance of an AP application 649 that is executable by the processor 641.

Although the sensor 604 is depicted as separate from the medical device 602, in various examples, the sensor 604 and medical device 602 may be incorporated into the same unit. That is, in various examples, the sensor 604 may be a part of the medical device 602 and contained within the same housing of the medical device 602 (e.g., the sensor 604 may be positioned within or embedded within the medical device 602). Glucose monitoring data (e.g., measured blood glucose values) determined by the sensor 604 may be provided to the medical device 602, smart device 607 and/or the personal diabetes management device 606 and may be used to perform the functions and deliver doses of insulin for automatic delivery of insulin by the medical device 602 as described with reference to the examples of FIGS. 1, 3A, 3B, 5A and 5B.

The sensor 604 may also be coupled to the user by, for example, adhesive or the like and may provide information or data on one or more medical conditions and/or physical attributes of the user. The information or data provided by the sensor 604 may be used to adjust drug delivery operations of the medical device 602.

In an example, the personal diabetes management device 606 may be a mobile computing device operable to manage a personal diabetes treatment plan via an AP application or an AID algorithm. The personal diabetes management device 606 may be used to program or adjust operation of the medical device 602 and/or the sensor 604. The personal diabetes management device 606 may be any portable electronic, computing device including, for example, a dedicated controller, such as PDM processor 661, a smartphone, or a tablet. In an example, the personal diabetes management device (PDM) 606 may include a PDM processor 661, a personal diabetes management device memory 663, and a communication device 664. The personal diabetes management device 606 may contain analog and/or digital circuitry that may be implemented as a PDM processor 661 (or controller) for executing processes to manage a user's blood glucose levels and for controlling the delivery of the drug or therapeutic agent to the user. The PDM processor 661 may also be operable to execute programming code stored in the personal diabetes management device memory 663. For example, the personal diabetes management device memory 663 may be operable to store an artificial pancreas (AP) application 669 that may be executed by the PDM processor 661. The PDM processor 661 may when executing the artificial pancreas application 669 may be operable to perform various functions, such as those described with respect to the examples in FIGS. 1, 3A, 3B, 5A and 5B. The wireless communication device 664 may be a device, such as a receiver, a transmitter, or a transceiver that operates according to one or more radio-frequency protocols. For example, the communication device 664 may include a cellular transceiver and a Bluetooth transceiver that enables the personal diabetes management device 606 to communicate with a data network (not shown) via the cellular transceiver and with the sensor 604 and the medical device 602. The respective transceivers of communication device 664 may be operable to transmit signals containing information useable by or generated by the AP application or the like. The communication devices 626, 646 and 676 of respective medical device 602, sensor 604 and Smart device 607 may also be operable to transmit signals containing information useable by or generated by the AP application or the like.

The medical device 602 may communicate with the sensor 604 over a wireless link 608 and may communicate with the personal diabetes management device 606 over a wireless link 631. The sensor 604 and the personal diabetes management device 606 may communicate over a wireless link 632. The smart device 607, when present, may communicate with the medical device 602, the sensor 604 and the personal diabetes management device 606 over wireless communication links 691, 692 and 693, respectively. The wireless communication links 608, 631, 632, 691, 692 and 693 may be any type of wireless link operating using known wireless standards or proprietary standards. As an example, the wireless communication links 608, 631, 632, 691, 692 and 693 may provide communication links based on Bluetooth®, Wi-Fi, a near-field communication standard, a cellular standard, or any other wireless protocol via the respective communication devices 626, 646 and 664. In some examples, the medical device 602 and/or the personal diabetes management device 606 may include a user interface 627, 678 and 668, respectively, such as a keypad, a touchscreen display, levers, buttons, a microphone, a speaker, a light, a display, or the like, that is operable to allow a user to enter information and allow the personal diabetes management device to output information for presentation to the user. Note that the respective user interface devices 627, 678 and 668 may serve with the associated hardware, such as a touchscreen display, as both an input device and an output device. For example, the user interface devices may present graphical user interfaces that guide a user, for example, through the presentation of prompts, to input information or provide data to the user as well as other functions.

In various examples, the drug delivery system 600 may implement the artificial pancreas (AP) algorithm (and/or provide AP functionality) to govern or control automatic delivery of insulin to a user (e.g., to maintain euglycemia—a normal level of glucose in the blood). The AP application (or an AID algorithm) may be implemented by the medical device 602 and/or the sensor 604. The AP application may be operable to determine an initial total daily insulin dosage as described with reference to the examples of FIGS. 1, 2, 4 and 5, as well as the times and incremental dosages of insulin delivery. In various examples, the AP application (or the AID algorithm) may determine the times and dosages for delivery based on information known about the user, such as the user's sex, age, weight, or height, and/or on information gathered about a physical attribute or condition of the user (e.g., from the sensor 604). For example, the AP application may determine an appropriate delivery of insulin based on glucose level monitoring of the user through the sensor 604. The AP application may also allow the user to adjust insulin delivery. For example, the AP application may allow the user to issue (e.g., via an input) commands to the medical device 602, such as a command to deliver an insulin bolus. In some examples, different functions of the AP application may be distributed among two or more of the personal diabetes management device 606, the medical device 602 or the sensor 604. In other examples, the different functions of the AP application may be performed by one device, such the personal diabetes management device 606, the medical device 602 or the sensor 604.

As described herein, the drug delivery system 600 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 600 or any constituent component thereof (e.g., the medical device 602 and/or the personal diabetes management device 606). The drug delivery system 600—for example, as an insulin delivery system implementing an AP application— may be considered to be a drug delivery system or an AP application-based delivery system that uses sensor inputs (e.g., data collected by the sensor 604).

In an example, one or more of the devices, 602, 604, 606 or 607 may be operable to communicate via a wireless communication link 688 with cloud-based services 611. The cloud-based services 611 may utilize servers and data storage (not shown). The communication link 688 may be a cellular link, a Wi-Fi link, a Bluetooth link, or a combination thereof, that is established between the respective devices 602, 604, 606 or 607 of system 600. The data storage provided by the cloud-based services 611 may store insulin delivery history related to the user, cost function data related to general delivery of insulin to users, or the like. In addition, the cloud-based services 611 may process anonymized data from multiple users to provide generalized information related to the various parameters used by the AP application.

In an example, the device 602 includes a communication device 664, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 611. For example, outputs from the sensor 604 or the medical device 602 may be transmitted to the cloud-based services 611 for storage or processing via the transceivers of communication device 664. Similarly, medical device 602, personal diabetes management device 606 and sensor 604 may be operable to communicate with the cloud-based services 611 via the communication link 688.

In an example, the respective receiver or transceiver of each respective device, 602, 606 or 607, may be operable to receive signals containing respective blood glucose measurement values of the number of blood glucose measurement values that may be transmitted by the sensor 604. The respective processor of each respective device 602, 606 or 607 may be operable to store each of the respective blood glucose measurement values in a respective memory, such as 623, 663 or 673. The respective blood glucose measurement values may be stored as data related to the artificial pancreas algorithm, such as 629, 649, 669 or 679. In a further example, the AP application operating on any of the personal diabetes management device 606, the Smart device 607, or sensor 604 may be operable to transmit, via a transceiver implemented by a respective communication device, 664, 674, 646, a control signal for receipt by a medical device. In the example, the control signal may indicate an amount of insulin to be expelled by the medical device 602.

Various operational scenarios and examples of processes performed by the system 600 are described herein. For example, the system 600 may be operable to implement the process examples of FIGS. 1, 4A, 4B, 5A and 5B.

The techniques described herein for providing functionality to set an adjusted total daily insulin factor and determine whether the adjusted total daily insulin factor exceeds a fixed algorithm delivery threshold. In response to a result of the determination, set a total daily insulin dosage using the attained information and obtain blood glucose measurement values over a period of time. Based on the obtained blood glucose measurement values, a level of glycated hemoglobin of a user may be determined. The set total daily insulin dosage may be modified to provide a modified total daily insulin dosage in response to the determined level of glycated hemoglobin. A control signal including the modified total daily insulin dosage may be output instructing a controller to actuate delivery of insulin according to the modified total daily insulin dosage.

For example, the system 600 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed delivery control application, AP application and algorithms may be operable to perform various functions related to open loop operations, such as modification of a pump mechanism rate or the like. Similarly, a dosage amount of insulin may be received by the AP application or algorithm from a user via a user interface. Other open-loop actions may also be implemented by adjusting user settings or the like in an AP application or algorithm.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein,"

respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A non-transitory computer readable medium embodied with programming code executable by a processor, and the processor when executing the programming code is operable to:
   receive a control instruction to deliver a dosage of a liquid drug, wherein the control instruction includes an amount of the liquid drug to be delivered during a control cycle;
   determine a number of pulses of a pump mechanism needed to output the dosage of the liquid drug included in the control instruction;
   modify a pump rate for delivery of the dosage of the liquid drug by adding additional time to provide an extended time period for outputting the dosage of the liquid drug during the control cycle; and
   output an actuation command to actuate a pump mechanism to output the dosage of the liquid drug included in the control instruction at the modified pump rate.

2. The non-transitory computer readable medium of claim 1, further embodied with programming code executable by the processor, and the processor, when executing the programming code to modify the pump rate, is further operable to:
   determine an increase in a delivery pressure value when outputting the dosage of the liquid drug in comparison to a respective delivery pressure value associated with a respective earlier output of the liquid drug; and
   use the determined increase in the delivery pressure value when modifying the pump rate.

3. The non-transitory computer readable medium of claim 2, further embodied with programming code executable by the processor, and the processor, when executing the programming code to determine the increase in the delivery pressure value, is further operable to:
   receive a pressure sensor signal from a pressure sensor coupled to a fluid delivery path through which the dosage of the liquid drug is output;
   based on the received pressure sensor signal, calculate an amount of delivery back pressure;
   determine whether the calculated amount of delivery back pressure exceeds a threshold; and
   based on a result of the determination, generate an indication that the delivery pressure value has increased.

4. The non-transitory computer readable medium of claim 2, further embodied with programming code executable by the processor, and the processor, when executing the programming code to determine the increase in the delivery pressure value, is further operable to:
   receive a pressure sensor signal from a pressure sensor in a fluid delivery path through which the dosage of the liquid drug is delivered, wherein a value in the received pressure sensor signal is representative of a pressure value;
   determine whether the pressure value exceeds a threshold;
   in response to the determination that the pressure value exceeds the threshold, access a lookup table containing pressure values with corresponding pump rates of output and corresponding additional time increments to select an additional time increment to be added to a preset time period, wherein the preset time period is an amount of time it takes the pump mechanism to output the dosage of the liquid drug after receipt of the actuation command;
   calculate the extended time period by adding the selected additional time increment to the preset time period; and
   use the extended time period in the modification of the pump rate.

5. The non-transitory computer readable medium of claim 4, further embodied with programming code executable by the processor, and the processor when executing the programming code is further operable to:
   based on the extended time period, determine a number of discrete actuation commands needed to output the dosage of the liquid drug; and
   output a respective actuation command after expiration of the selected additional time added to the preset time period.

6. The non-transitory computer readable medium of claim 1, wherein:
   the pump mechanism is operable to output a fixed amount of insulin during each pulse of the pump mechanism that ends with the preset time period.

7. The non-transitory computer readable medium of claim 1, wherein:
   a pump resolution is a fixed amount of the liquid drug the pump mechanism delivers in a pump mechanism pulse, wherein a pump mechanism pulse is generated in response to the actuation command, and
   the number of pump mechanism pulses needed to deliver the dosage of the liquid drug is equal to the dosage of the liquid drug divided by the pump resolution, and
   the programming code is executed by the processor to determine the number of pulses of the pump mechanism needed to output the dosage of the liquid drug included in the control instruction, is further executable to cause the processor to:
   divide a control cycle by the number of pulses of the pump mechanism to obtain an output distribution, wherein the output distribution the dosage of the liquid drug over the control cycle;
   use the output distribution to determine timing of delivery of partial doses of the dosage of the liquid drug; and
   generate a respective actuation command to actuate the pump mechanism to output each partial dose of the partial doses distributed over the output distribution.

8. A drug delivery device, comprising:
   a reservoir operable to hold a liquid drug;
   a cannula coupled to the reservoir via a fluid delivery path and operable to output the liquid drug to a user;
   a pump mechanism coupled to the reservoir and operable to output the liquid drug from the reservoir via the fluid delivery path and out of the cannula;
   a memory operable to store programming code, applications including a delivery control application, and data;
   a controller communicatively coupled to the pump mechanism and the memory, and operable to execute programming code and the applications including the delivery control application; and a communication device operable to wirelessly communicate with an external device and communicatively coupled to the controller, wherein:

the controller, when executing the delivery control application, is operable to:

receive, from the external device, a control instruction including a dosage of the liquid drug to be output by the pump mechanism, wherein the received control instruction indicates an amount of the liquid drug to be output for a control cycle;

calculate an output distribution of the dosage of the liquid drug by the pump mechanism, wherein the output distribution is a series of partial liquid drug doses output at discrete times distributed over the control cycle; and output an actuation command to actuate the pump mechanism to deliver a partial liquid drug dose in the series of partial liquid drug doses.

9. The device of claim 8, wherein the controller, when executing the delivery control application and calculating the output distribution, is further operable to:

determine a number of times the pump mechanism needs to actuate to output the dosage of the liquid drug included in the control instruction;

segment the control cycle into time segments by dividing the control cycle by the determined number of times the pump mechanism ought to actuate; and use the time segments to generate the actuation command.

10. The device of claim 9, wherein the controller, when executing the delivery control application and determining the number of times the pump mechanism needs to actuate, is further operable to:

divide the dosage of the liquid drug by a resolution of the pump mechanism to produce the number of times the pump needs to be actuated to output the series of partial liquid drug doses.

11. The device of claim 10, wherein the resolution of the pump mechanism is an amount of the liquid drug that the pump mechanism delivers upon each actuation.

12. The device of claim 9, wherein the controller, when executing the delivery control application, is further operable to:

output the actuation command at a beginning of each respective time segment of the control cycle.

13. The device of claim 8, further comprising:

a pressure sensor coupled to the controller and operable to detect pressure associated with the liquid drug in the fluid delivery path and deliver a pressure sensor signal related to the detected pressure to the controller, and wherein the controller is further operable to:

determine based on a pressure sensor signal received from the pressure sensor that a delivery pressure value has increased; and in response to determining the increase in the delivery pressure value, begin calculating the output distribution.

14. The device of claim 13, wherein the controller, when determining the increase in the delivery pressure value, is further operable to:

receive the pressure sensor signal from the pressure sensor coupled to a fluid delivery path through which the dosage of the liquid drug is output;

based on the received pressure sensor signal, calculate an amount of delivery back pressure;

determine whether the calculated amount of delivery back pressure exceeds a threshold; and based on the result of the determination, generate an indication that the delivery pressure value has increased.

15. A method, comprising:

receiving a control instruction to deliver a dosage of a liquid drug, wherein the control instruction includes a dosage of the liquid drug to be output as a pump mechanism;

determining a plurality of doses of the liquid drug, a sum of which equals the dosage of the liquid drug, to be delivered based on a duration of a control cycle; and outputting a series of actuation commands, wherein:

the series of actuation commands includes a number of actuation commands equal to a number of doses of the liquid drug in the plurality of doses of the liquid drug, each actuation command in the series of actuation commands actuates a pump mechanism to output a respective dose of the liquid drug of the plurality of doses of the liquid drug, and each actuation command is applied after passage of a selected additional time period based on the duration of the control cycle.

16. The method of claim 15, comprising:

determining an increase in a delivery pressure value when outputting the liquid drug in comparison to a respective delivery pressure value associated with a respective earlier output of the liquid drug; and using the determined increase in the delivery pressure value when determining the plurality of doses of the liquid drug.

17. The method of claim 16, wherein determining the increase in the delivery pressure value, comprises:

receiving a pressure sensor signal from a pressure sensor coupled to a fluid delivery path through which the dosage of the liquid drug is output;

based on the received pressure sensor signal, calculating an amount of delivery back pressure;

determining whether the calculated amount of delivery back pressure exceeds a threshold; and based on the result of the determination, generating an indication that the deliver pressure value has increased.

18. The method of claim 15, further comprising:

in response to the control instruction, calculating a number of pump mechanism pulses needed to deliver the dosage of the liquid drug, wherein:

a pump resolution is a fixed amount of insulin the pump mechanism delivers in a pump mechanism pulse, wherein a pump mechanism pulse is an actuation of the pump mechanism for a preset time period, and the number of pump mechanism pulses needed to deliver the dosage of the liquid drug is equal to the dosage of the liquid drug divided by the pump resolution, dividing a control cycle by the number of pump mechanism pulses to obtain an output distribution of the dosage of the liquid drug over the control cycle; and use the output distribution and the number of pump mechanism pulses to determine when to apply the actuation command to the pump mechanism.

19. The method of claim 15, further comprising:

determining a number of discrete actuation commands needed to output the dosage of the liquid drug; and wherein outputting the series of actuation commands includes:

outputting a respective actuation command of the series of actuation commands after expiration of the selected additional time added to a preset time period, wherein the preset time period is an amount of time it takes the pump mechanism to output a dose of liquid drug of the plurality of doses of the liquid drug in response to receipt of the actuation command.

20. The method of claim 15, further comprising:

determining a number of pump mechanism pulses needed to output the dosage of the liquid drug included in the control instruction, wherein the pump mechanism is operable to output a fixed amount of liquid drug in a preset time period during each respective pump mechanism pulse.

* * * * *